(12) United States Patent
Dolan et al.

(10) Patent No.: US 6,220,256 B1
(45) Date of Patent: *Apr. 24, 2001

(54) DENTAL FLOSS HOLDER AND IMPROVED DENTAL FLOSS

(75) Inventors: John Dolan, Boothwyn, PA (US); Michael Zumbrum, Rising Sun, MD (US)

(73) Assignee: Gore Enterprise Holdings, Inc., Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,684

(22) Filed: Feb. 19, 1999

Related U.S. Application Data

(63) Continuation-in-part of application No. 08/958,784, filed on Oct. 27, 1997, now Pat. No. 5,975,296.

(51) Int. Cl.⁷ .................................................. A61C 15/20
(52) U.S. Cl. .................................... 132/323; 132/325
(58) Field of Search ................................. 132/323, 325, 132/326, 327, 328, 321; 206/63.5, 368; 51/296, 308; 606/231, 148

(56) References Cited

U.S. PATENT DOCUMENTS

| | | | |
|---|---|---|---|
| D. 237,499 | 11/1975 | Maloney et al. | D24/99 |
| D. 244,376 | 5/1977 | Chodorow . | |
| D. 244,609 | 6/1977 | Chodorow . | |
| D. 250,214 | 11/1978 | Chodorow . | |
| D. 251,074 * | 2/1979 | Schiff | 132/323 |
| D. 251,075 | 2/1979 | Schiff . | |
| D. 285,369 | 8/1986 | Morin et al. | D28/64 |
| D. 291,412 | 8/1987 | Chodorow et al. . | |
| D. 309,041 | 7/1990 | Schneider | D28/64 |
| D. 310,582 | 9/1990 | Kujirai | D28/64 |
| D. 348,332 | 6/1994 | Haggett-King et al. | D28/64 |
| D. 356,394 | 3/1995 | Daugherty | D28/64 |
| D. 374,311 | 10/1996 | Dolan et al. | D28/64 |
| D. 374,744 | 10/1996 | Dolan et al. | D28/64 |
| D. 401,701 | 11/1998 | Chodorow . | |
| D. 408,589 | 4/1999 | Chodorow . | |

(List continued on next page.)

FOREIGN PATENT DOCUMENTS

| | | |
|---|---|---|
| 1095460 | 12/1960 | (DE) . |
| 3920256 | 2/1990 | (DE) . |
| 0 611 533 | 8/1994 | (EP) . |
| 2 278 283 | 11/1994 | (GB) . |
| WO 97/24078 | 7/1997 | (WO) . |
| WO 97/28898 | 8/1997 | (WO) . |
| WO 98/01082 | 1/1998 | (WO) . |

*Primary Examiner*—Gene Mancene
*Assistant Examiner*—Pedro Philogene
(74) *Attorney, Agent, or Firm*—Allan M. Wheatcraft

(57) ABSTRACT

A dental floss holder including a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a first position in which the first end portions of the arms diverge away from one another, and a second position in which the first end portions are moved toward one another. Dental floss material has one end secured to the first end portion of one arm and an opposite end secured to the first end portion of the other arm. The dental floss material has a first tension when the first end portions are in their spaced apart position and a second tension when the first end portions are moved toward one another, said first tension being greater than the second tension. Also disclosed is a filament, such as a dental floss, that contains fumed silica. The dental floss may be used alone or with the disclosed dental floss holder.

48 Claims, 12 Drawing Sheets

U.S. PATENT DOCUMENTS

| | | |
|---|---|---|
| 788,947 | 5/1905 | Roth . |
| 1,110,680 | 9/1914 | Gamble . |
| 1,415,765 | 5/1922 | Bailey . |
| 1,618,351 | 2/1927 | Raycraft . |
| 1,627,525 | 5/1927 | Munro . |
| 1,916,653 | 7/1933 | Bodde . |
| 2,354,454 | 7/1944 | Geffner ................................. 132/91 |
| 2,384,712 | 9/1945 | Turenchalk et al. . |
| 2,443,415 | 6/1948 | Buscarino . |
| 2,702,555 | 2/1955 | DeMar . |
| 2,735,436 | 3/1955 | Russo ................................... 132/91 |
| 2,811,162 | 10/1957 | Brody . |
| 3,016,304 | 1/1962 | Preston et al. . |
| 3,533,420 | 10/1970 | Maloney et al. ...................... 132/92 |
| 3,592,203 | 7/1971 | Johnson ............................... 132/91 |
| 3,631,869 | 1/1972 | Espinosa . |
| 3,693,638 | 9/1972 | Ciccarelli . |
| 3,699,979 | 10/1972 | Muhler et al. . |
| 3,783,883 | 1/1974 | Alexander . |
| 3,800,812 | 4/1974 | Jaffe . |
| 3,834,404 | 9/1974 | Chien .................................. 132/91 |
| 3,838,702 | 10/1974 | Standish et al. . |
| 3,882,879 | 5/1975 | Lucas ................................... 132/92 |
| 3,892,249 | 7/1975 | Jones et al. . |
| 3,897,795 | 8/1975 | Engel . |
| 3,910,294 | 10/1975 | Reed . |
| 3,913,927 | 10/1975 | Day ..................................... 132/92 |
| 3,915,178 | 10/1975 | Zellers ................................. 132/92 |
| 3,926,201 | 12/1975 | Katz . |
| 3,949,769 | 4/1976 | Minka .................................. 132/91 |
| 3,953,566 | 4/1976 | Gore . |
| 3,960,159 | 6/1976 | Tesberg ............................... 132/90 |
| 4,005,721 | 2/1977 | Yasumoto ............................. 132/91 |
| 4,006,750 | 2/1977 | Chodorow . |
| 4,008,728 | 2/1977 | Sanchez ............................... 132/92 |
| 4,014,354 | 3/1977 | Garrett ................................. 132/91 |
| 4,016,892 | 4/1977 | Chodorow ............................ 132/91 |
| 4,022,229 | 5/1977 | Minka .................................. 132/92 |
| 4,029,453 | 6/1977 | Campion . |
| 4,031,909 | 6/1977 | Kelley .................................. 132/91 |
| 4,041,962 | 8/1977 | Johannsson et al. .................. 132/91 |
| 4,052,994 | 10/1977 | Thun ................................... 132/92 |
| 4,162,687 | 7/1979 | Lorch .................................. 132/91 |
| 4,192,330 | * 3/1980 | Johnson ............................... 132/323 |
| 4,206,774 | 6/1980 | Griparis ............................... 132/92 |
| 4,510,934 | * 4/1985 | Batra ................................... 606/231 |
| 4,522,216 | 6/1985 | Bunker ................................ 132/92 |
| 4,556,074 | 12/1985 | Morin et al. ......................... 206/53 |
| 4,615,349 | 10/1986 | Kukuruzinski ....................... 132/91 |
| 4,655,233 | 4/1987 | Laughlin .............................. 132/91 |
| 4,655,234 | 4/1987 | Bowden ............................... 132/92 |
| 4,671,307 | 6/1987 | Curbow et al. ...................... 132/91 |
| 4,729,392 | 3/1988 | Tenny .................................. 132/91 |
| 4,736,757 | 4/1988 | Badoux ................................ 132/91 |
| 4,738,271 | 4/1988 | Bianco ................................. 132/92 |
| 4,790,336 | 11/1988 | Kuo .................................... 132/325 |
| 4,807,752 | 2/1989 | Chodorow ........................... 206/63.5 |
| 4,830,032 | 5/1989 | Jousson ............................... 132/323 |
| 4,832,032 | 5/1989 | Grollimund et al. ................. 132/327 |
| 4,883,080 | 11/1989 | Lang ................................... 132/332 |
| 4,936,326 | 6/1990 | Eckroat ............................... 132/326 |
| 4,966,176 | 10/1990 | Lachenberg ......................... 132/325 |
| 4,982,752 | 1/1991 | Rodriguez . |
| 4,996,056 | 2/1991 | Blass . |
| 5,033,488 | 7/1991 | Curtis et al. . |
| 5,060,681 | 10/1991 | Westbrook et al. ................... 132/325 |
| 5,113,880 | 5/1992 | Honda et al. . |
| 5,114,438 | * 5/1992 | Leatherman et al. ................. 51/296 |
| 5,123,432 | 6/1992 | Wyss . |
| 5,127,415 | 7/1992 | Preciutti ............................... 132/323 |
| 5,147,722 | 9/1992 | Koslow ................................ 428/402 |
| 5,176,157 | 1/1993 | Mazza ................................. 132/322 |
| 5,188,133 | 2/1993 | Romanus ............................. 132/325 |
| 5,197,498 | 3/1993 | Stewart ................................ 132/325 |
| 5,209,251 | 5/1993 | Curtis et al. . |
| 5,220,932 | 6/1993 | Blass . |
| 5,253,662 | 10/1993 | Won .................................... 132/325 |
| 5,262,234 | 11/1993 | Minor et al. . |
| 5,279,314 | 1/1994 | Poulos et al. ........................ 132/322 |
| 5,280,797 | 1/1994 | Fry ...................................... 132/323 |
| 5,287,865 | 2/1994 | Fulton ................................. 132/323 |
| 5,323,796 | 6/1994 | Urso .................................... 132/322 |
| 5,375,615 | 12/1994 | Wahlstrom ........................... 132/325 |
| 5,400,811 | 3/1995 | Meibauer ............................. 132/322 |
| 5,411,041 | 5/1995 | Ritter ................................... 132/322 |
| 5,433,227 | 7/1995 | Chen . |
| 5,518,012 | 5/1996 | Dolan et al. . |
| 5,538,023 | * 7/1996 | Oczkowski et al. .................. 132/323 |
| 5,566,691 | 10/1996 | Dolan et al. . |
| 5,573,021 | 11/1996 | Grofcisk et al. ..................... 132/324 |
| 5,657,779 | 8/1997 | Blass et al. . |
| 5,657,780 | 8/1997 | Giacopuzzi . |
| 5,664,592 | 9/1997 | Regnier . |
| 5,692,531 | 12/1997 | Chodorow . |
| 5,695,879 | * 12/1997 | Goldmann et al. ................... 428/364 |
| 5,697,390 | 12/1997 | Garrison et al. . |
| 5,707,734 | 1/1998 | Hawkins et al. . |
| 5,780,126 | * 7/1998 | Smith et al. ......................... 428/34.5 |
| 5,819,769 | 10/1998 | Gutierrez . |
| 5,829,458 | * 11/1998 | Chodorow ........................... 132/323 |

\* cited by examiner

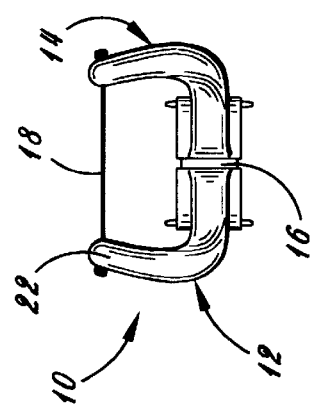
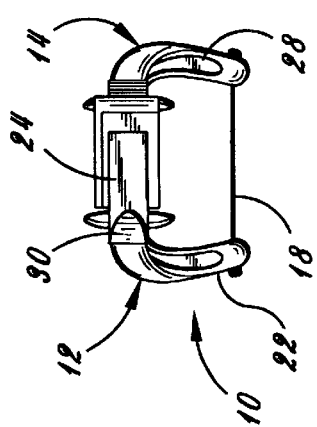
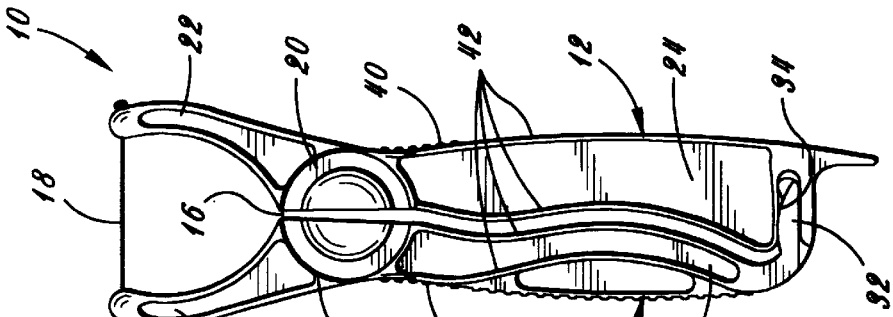
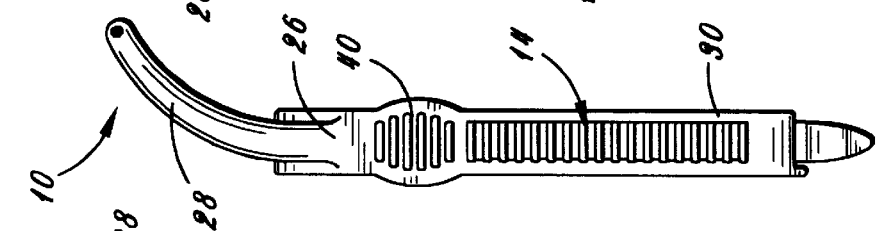
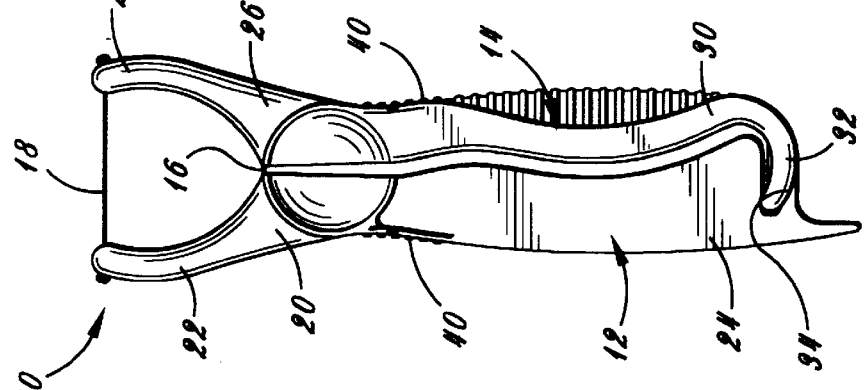
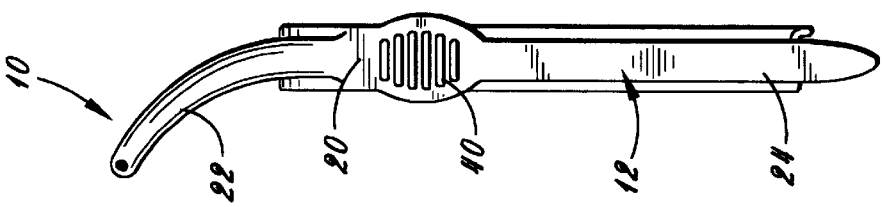

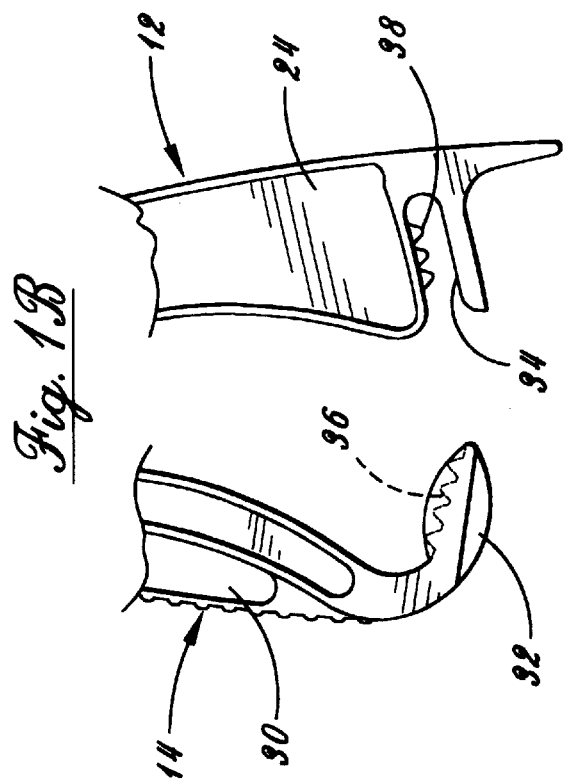
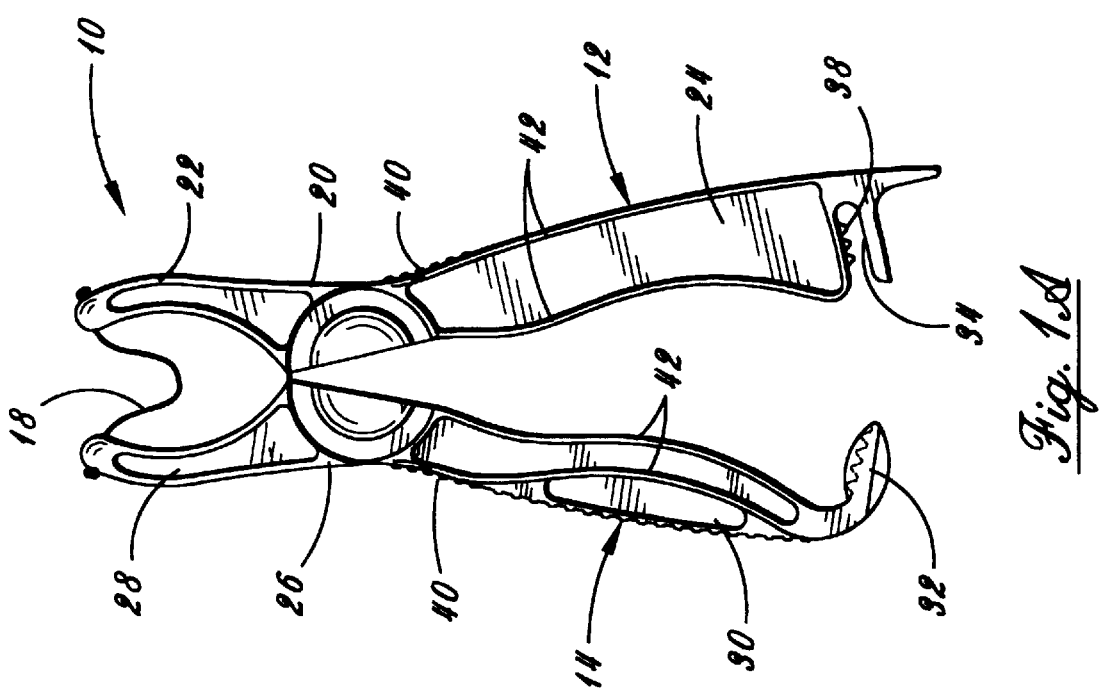

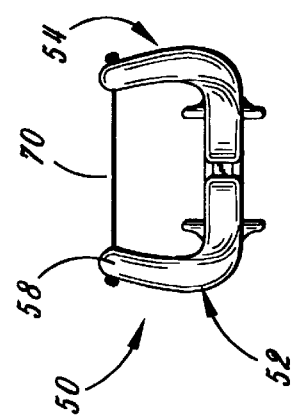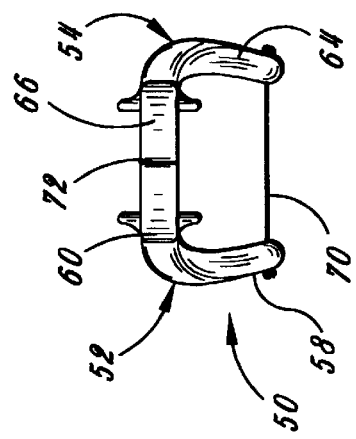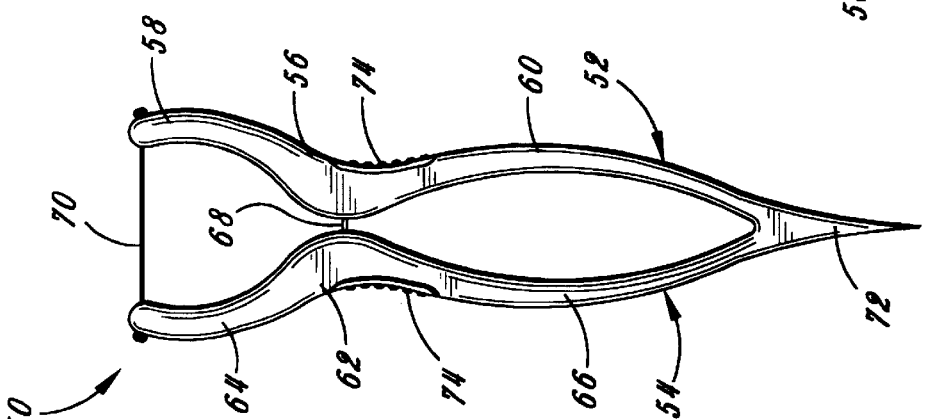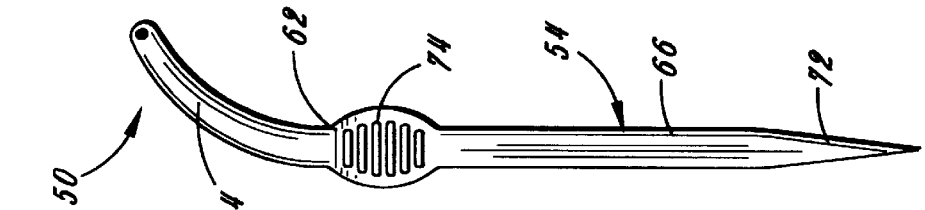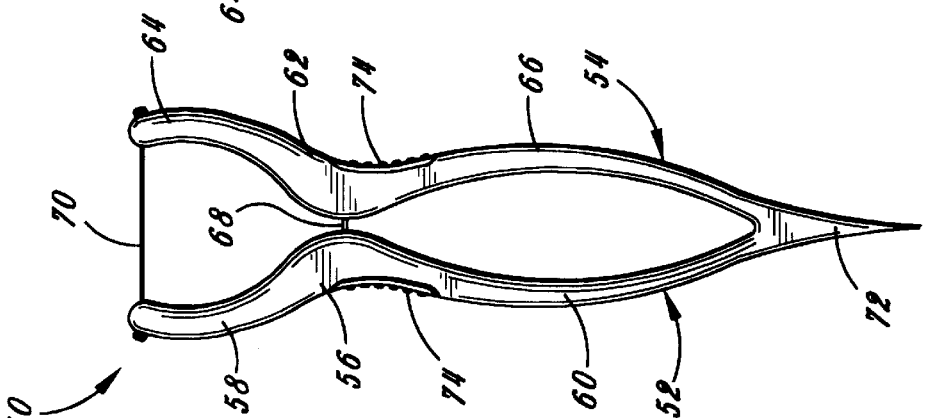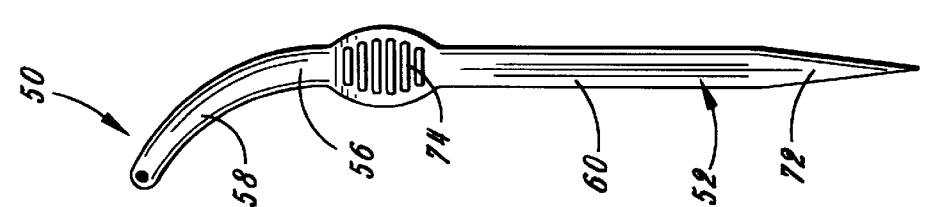

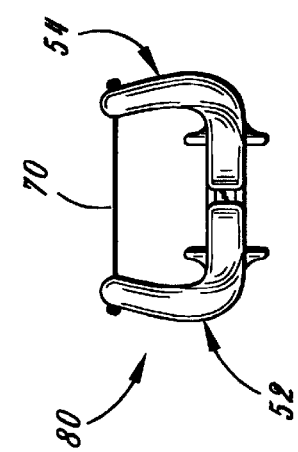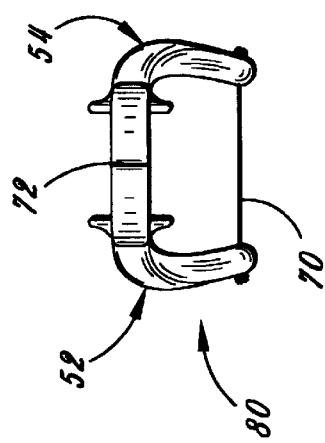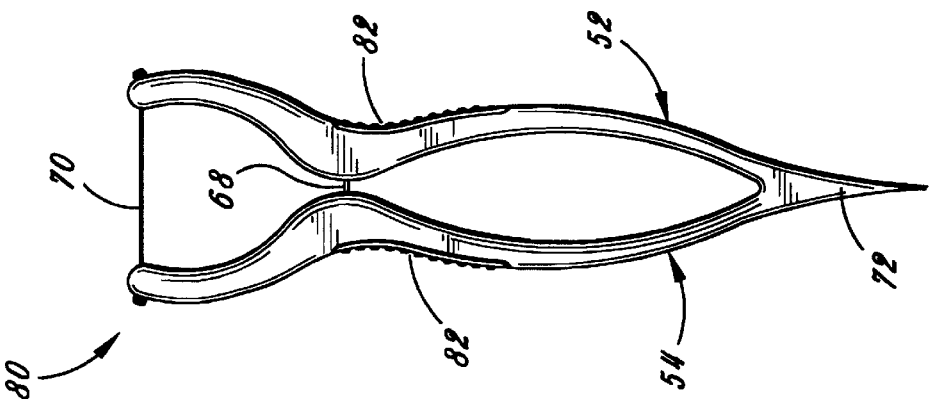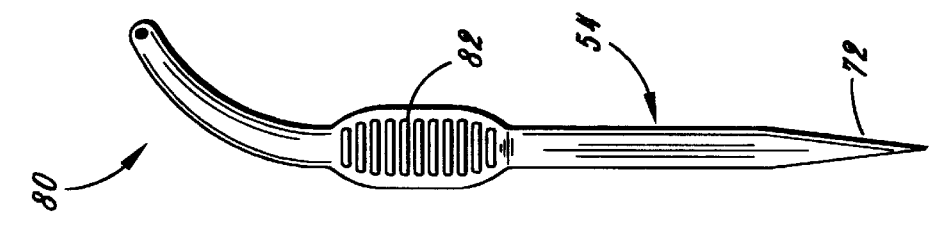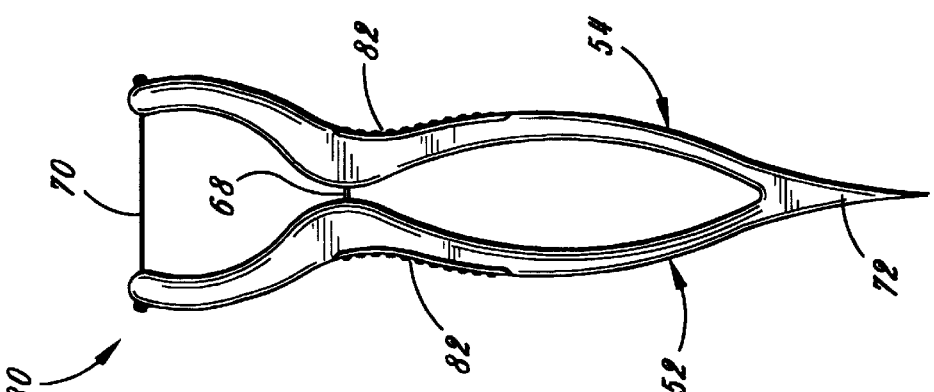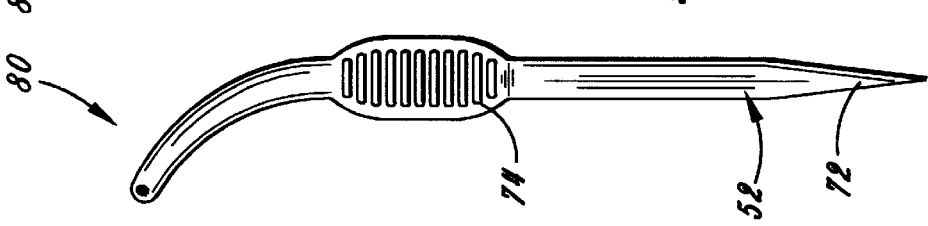

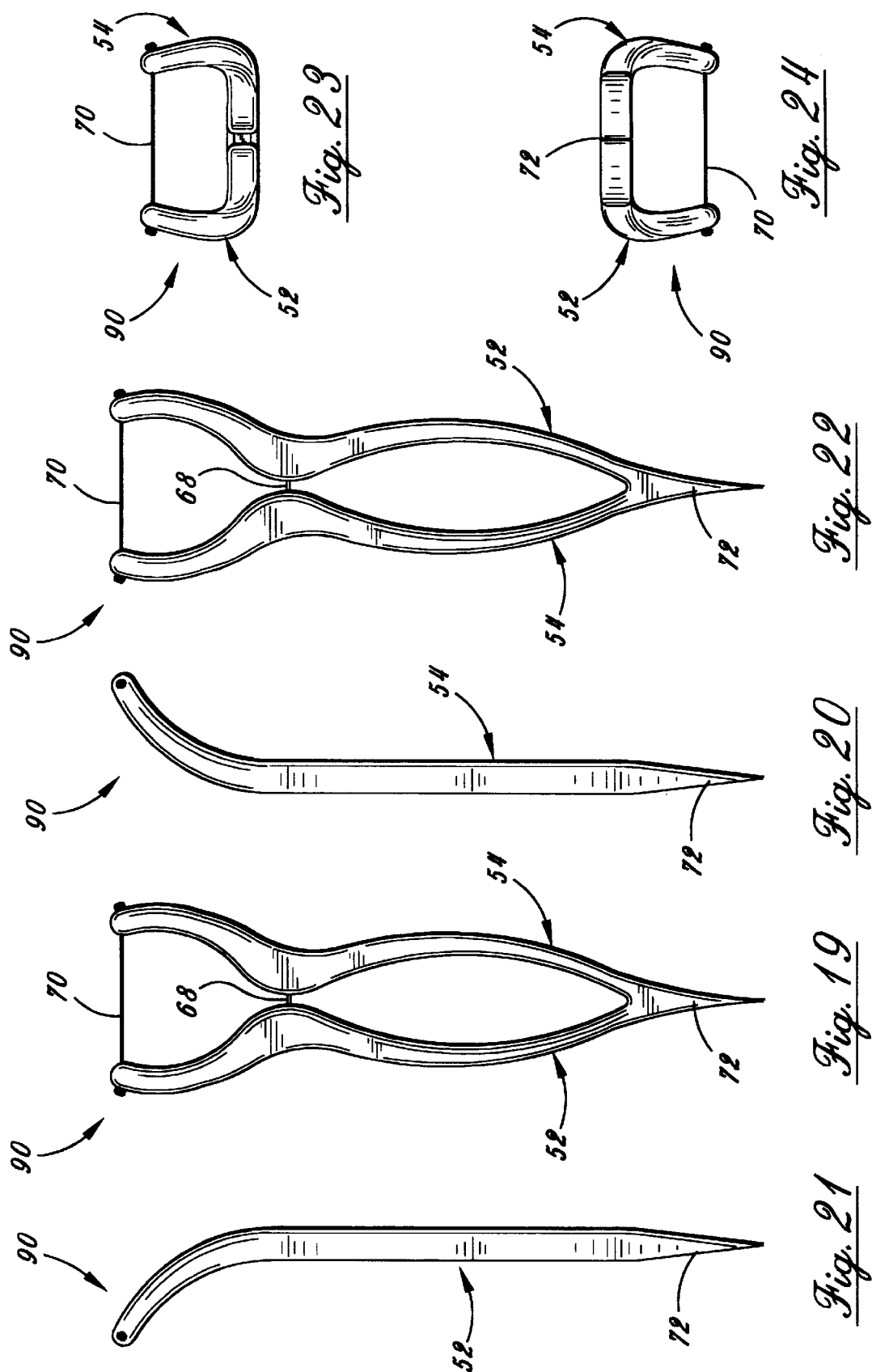

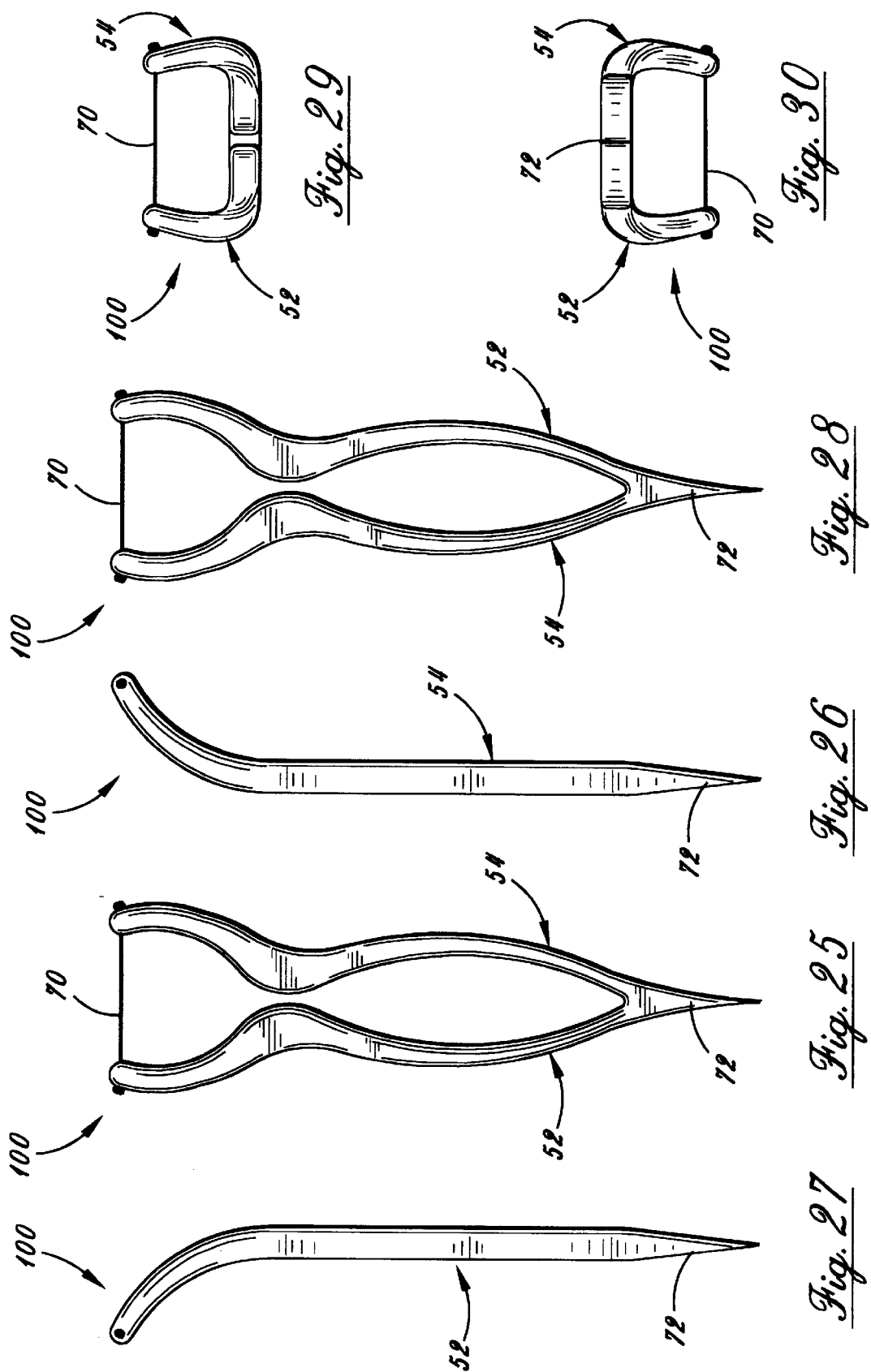

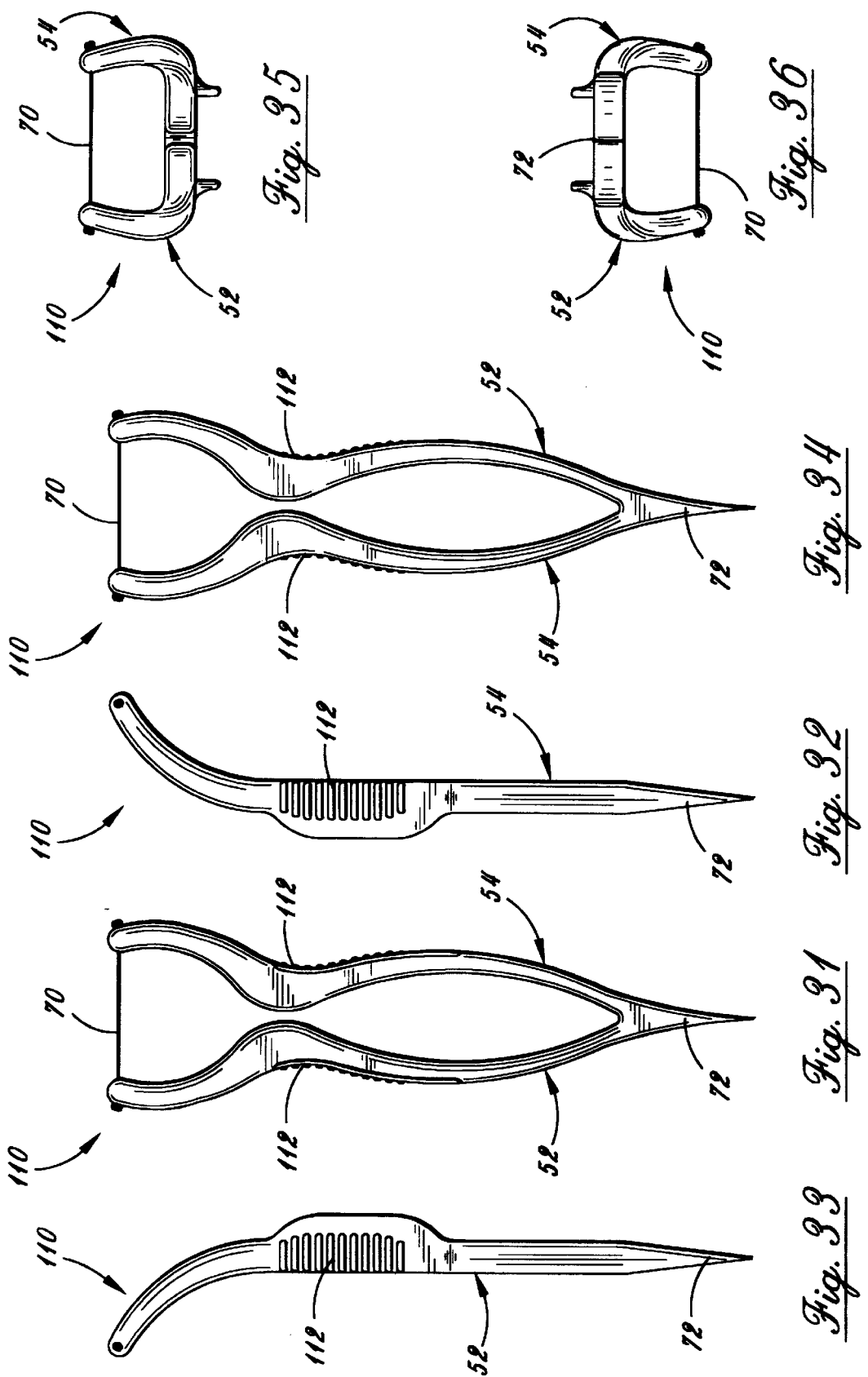

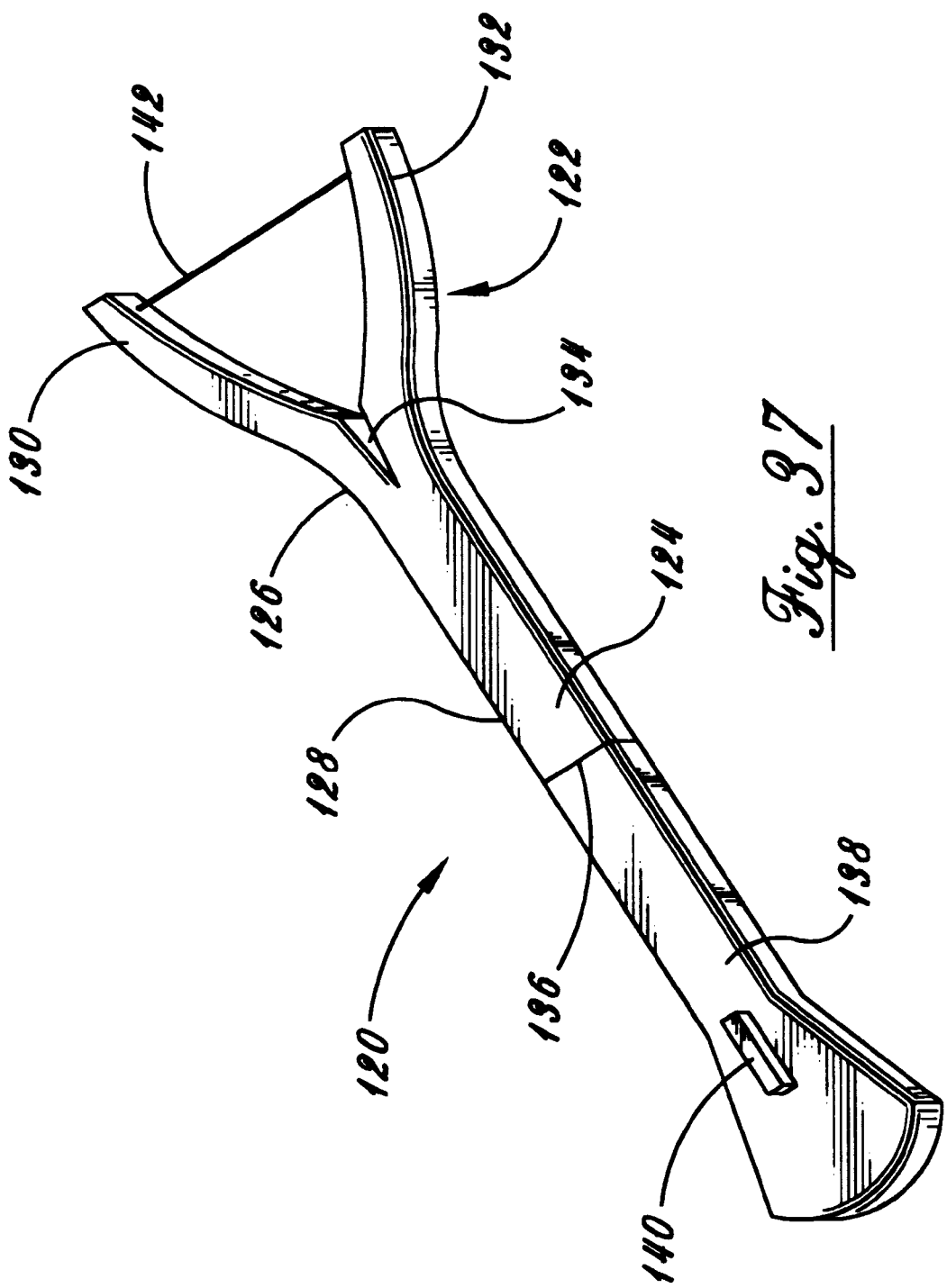

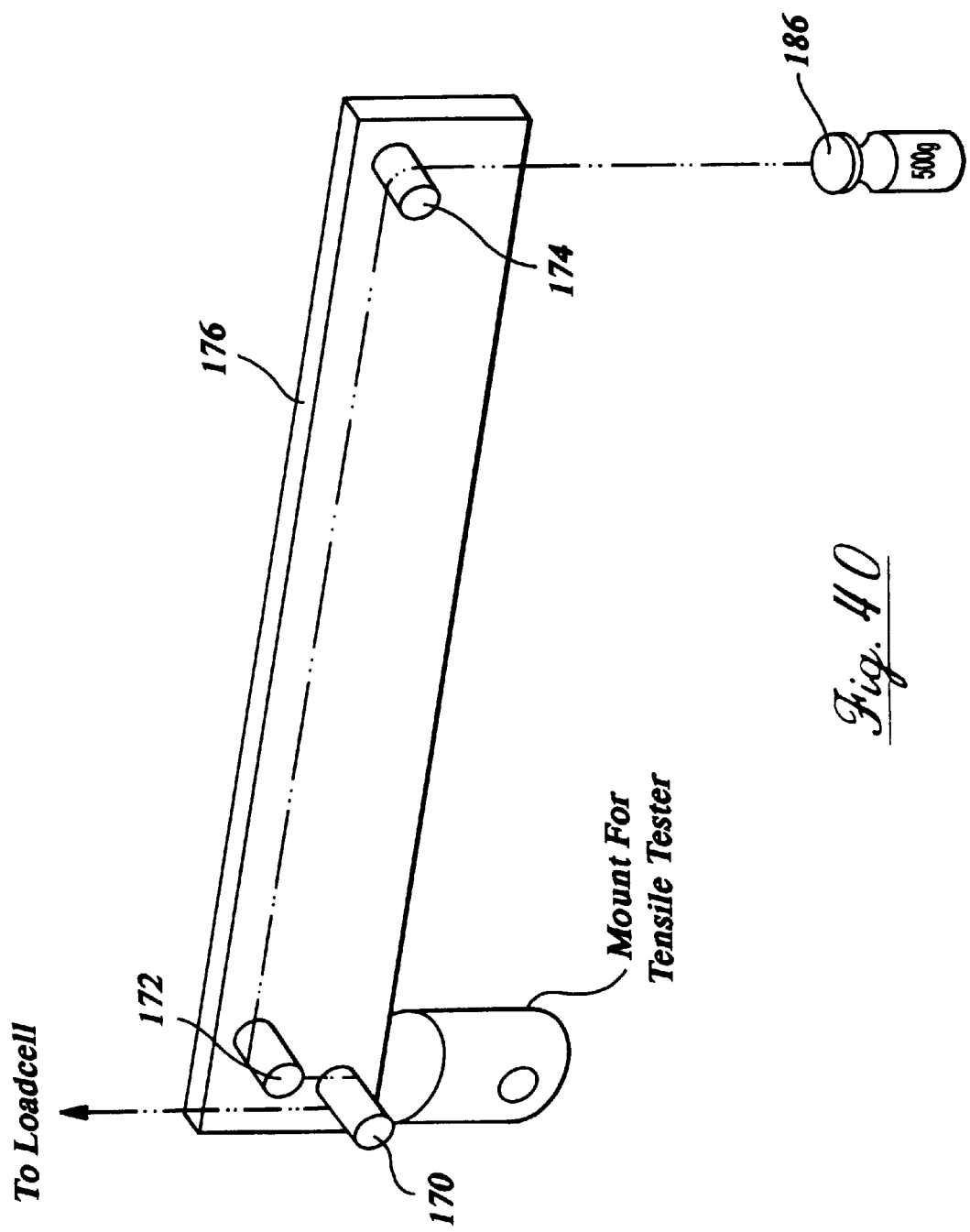

DENTAL FLOSS HOLDER AND IMPROVED DENTAL FLOSS

RELATED APPLICATIONS

This application is a continuation-in-part of U.S. patent application Ser. No. 08/958,784, filed Oct. 27, 1997. Now U.S. Pat. No. 5,975,296.

FIELD OF THE INVENTION

This invention generally relates to dental floss and to dental floss holders. More particularly, the present invention relates to a novel single use dental floss holder which is capable of, among other things, adjusting the tension of dental floss held by the holder, and to an improved dental floss that may be used alone or with the holder.

BACKGROUND OF THE INVENTION

Dental floss holders are well known in the art. Such a prior art holder typically comprises a body having a linear portion for grasping the holder and a generally U-shaped or V-shaped end portion defined by a pair of fingers or tines which hold a string of dental floss material therebetween. The dental floss is securely fixed to the tines at opposite ends thereof by any well known manner. This construction of the dental floss holder enables the user to hold the linear portion while manipulating the dental floss between the user's teeth.

While the dental floss holder described above is suitable for its intended use, it does suffer from several disadvantages. For instance, prior to using the dental floss holder, the dental floss is fixed so that it can be manipulated between teeth. However, after forcing the dental floss many times between adjacent teeth, the dental floss stretches and becomes slack, thereby losing some of its initial tension. This makes it more difficult to manipulate the dental floss between teeth.

Additionally, during flossing of teeth, it is preferred to maintain the dental floss taut when initially inserting the floss between teeth, and, upon entering the space between the teeth, lessening the tension so that the dental floss wraps around the tooth being flossed. With the prior art dental floss holder described above, this preferred method of flossing one's teeth is impossible since the dental floss maintains only one tension, albeit this tension lessens as the dental floss holder is manipulated between one's teeth.

Another limitation of previous dental floss holders is that the floss is relatively easily pulled out of the holder, rendering the holder useless. A floss that can be held more securely by the holder, or by a user's hands, is desirable.

The foregoing illustrates some limitations known to exist in present dental floss holders. Thus, it is apparent that it would be advantageous to provide an improved dental floss holder and dental floss directed to overcoming one or more of the limitations set forth above. Accordingly, suitable alternatives are provided including features more fully disclosed hereinafter.

SUMMARY OF THE INVENTION

The present invention advances the art of dental floss, dental floss holders, and the techniques for creating same, beyond those previously known.

In one embodiment of the present invention, a dental floss holder comprises a pair of arms or tines, each arm having a middle portion and first and second opposite end portions. The first end portion of each arm curves outwardly away from its respective middle portion wherein the middle portions of the arms are positioned proximate one another so as to define a pivot. The curvature permits the user to easily manipulate the dental floss device deep in the oral cavity without requiring the user to open his or her mouth extremely wide. Additionally, the area encompassing the yoke section, which is defined as the tines and the dental floss, is sufficiently large to permit the user to easily pass the dental floss around the molars. The second end portions are movable between a spaced apart position in which the second end portions of the arms diverge away from one another, and a proximate position in which the second end portions are moved toward one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension.

In a second embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. Connecting means releasably connects terminal ends of the second end portions of the arms to one another. Hence, the tension within the floss material is maintained. The connecting means located at the terminal ends may have a tooth configurations such to provide a connecting condition where the user may engage one tooth or several teeth of the locking means, hence resulting in varying tensioning of the dental floss as desired.

In a third embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. A living hinge is provided for connecting the middle portions of the arms to one another. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. A finger gripping surface is further provided on the second end portion of each arm to receive fingers of the user. Each finger gripping surface is located adjacent its respective middle portion of the arm.

In a fourth embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. The second end portions of the arms are integrally formed with one another at respective terminal ends thereof. The terminal ends of the second end portions of the arms define a pointed member for stimulating a gingival area of an oral cavity. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension.

In a fifth embodiment of the present invention, the dental floss holder comprises a pair of arms, each arm having a middle portion and first and second opposite end portions. The first end portion of each arm curves outwardly away from its respective middle portion wherein the middle portions of the arms are positioned proximate one another so as to define a pivot. The second end portions are movable between a spaced apart position in which the second end portions of the arms diverge away from one another, and a proximate position in which the second end portions are moved toward one another. The first end portions of the arms project rearwardly from the middle and second end portions. Dental floss material has one end secured to the first end portion of one arm and an opposite end secured to the first end portion of the other arm. The dental floss material has a first tension when the second end portions are in their spaced apart position and a second tension when the second end portions are in their proximate position, the second tension being greater than the first tension. A finger gripping surface is further provided on the second end portion of each arm to receive fingers of the user. The finger gripping surface is located adjacent the middle portion of the arm wherein it projects forwardly with respect to the first and second end portions.

In another aspect, the present invention provides a filament in the form of a polytetrafluoroethylene filament containing fumed silica. The filament is useful as a dental floss, a medical suture, a sewing thread, and in filter bags. The fumed silica is present in the filament in an amount of greater than about 1% by weight (of fumed silica to polytetrafluoroethylene), with preferred amounts of greater than 2%, greater than 3%, greater than 4%, greater than 5%, and greater than 10%. More preferably, the fumed silica is present in the filament in an amount by weight of about 5%, about 10%, or about 20%. The filament has a strength of greater than 1 gram per denier, with preferred strengths of greater than 2 grams per denier, greater than 3 grams per denier, and greater than 4 grams per denier. The fumed silica in the filament has a primary particle size that averages less than 25 nanometers.

In another aspect, the filament is a dental floss having a plurality of layers of polytetrafluoroethylene, with at least one of the layers having fumed silica disposed in it. Preferably, the filament has an inner layer and two outer layers, with the fumed silica disposed in at least one of the two outer layers.

In still another aspect, the invention provides a dental floss holder including a pair of arms, each arm having a middle portion and first and second opposite end portions, the first end portion of each arm curving outwardly away from its respective middle portion, the middle portions of the arms being positioned proximate one another so as to define a pivot, the second end portions being movable between a first position in which the first end portions of the arms diverge away from one another, and a second position in which the first end portions are moved toward one another; and dental floss material having one end secured to the first end portion of one arm and an opposite end secured to the first end portion of the other arm, the dental floss material having a first tension when the first end portions are in their spaced apart position and a second tension when the first end portions are moved toward one another, the first tension being greater than the second tension; wherein the dental floss material is a filament of polytetrafluoroethylene containing fumed silica.

In still another aspect, the invention provides a dental floss made by a process comprising providing an aqueous PTFE dispersion, adding fumed silica to the dispersion to form a mixture, cocoagulating the mixture to form a cocoagulate, drying the cocoagulate, extruding the cocoagulate into a tape, cutting the tape into filaments to form the dental floss, and expanding the filaments to increase tensile strength.

It is, therefore, a purpose of the present invention to provide a dental floss holder in which the tension of dental floss held by the holder can be manipulated to achieve a desired tension for increasing the effectiveness of flossing.

A further purpose of the present invention is to provide a dental floss holder in which the tension of the dental floss can be adjusted and locked at a certain tension.

Another purpose of the present invention is to provide a dental floss holder which is easy to use and manipulate by hand.

Yet another purpose of the present invention is to provide a dental floss holder which can be used to stimulate a gingival area of an oral cavity.

A further purpose of the present invention is to provide a dental floss holder which simple in design and cost-efficient to manufacture.

Still another purpose of the present invention is to provide a dental floss that is grippable by a floss holder, or by a user, such that the floss is not easily pulled out of the holder.

BRIEF DESCRIPTION OF THE DRAWINGS

The foregoing summary, as well as the following detailed description of preferred embodiments of the invention, will be better understood when read in conjunction with the appended drawings. For purposes of illustrating the invention, there are shown in the drawings embodiments which are presently preferred. It should be understood, however, that the invention is not limited to the precise arrangement and instrumentality shown. In the drawings:

FIG. 1 is a front elevational view of a dental floss holder of a first preferred embodiment of the present invention;

FIG. 1A is a rear elevational view of the dental floss holder in which second end portions of arms of the dental floss holder are illustrated in a spaced apart position;

FIG. 1B is an enlarged fragmentary view of the second end portions of the arms of the dental floss holder;

FIG. 2 is a right side elevational view of the dental floss holder illustrated in FIG. 1;

FIG. 3 is a left side elevational view thereof;

FIG. 4 is a rear elevational view thereof;

FIG. 5 is a top plan view thereof;

FIG. 6 is a bottom plan view thereof;

FIG. 7 is a front elevational view of a dental floss holder of a second preferred embodiment;

FIG. 8 is a right side elevational view of the dental floss holder illustrated in FIG. 7;

FIG. 9 is a left side elevational view thereof;

FIG. 10 is a rear elevational view thereof;

FIG. 11 is a top plan view thereof;

FIG. 12 is a bottom plan view thereof;

FIG. 13 is a front elevational view of a dental floss holder of a third preferred embodiment;

FIG. 14 is a right side elevational view of the dental floss holder illustrated in FIG. 13;

FIG. 15 is a left side elevational view thereof;

FIG. 16 is a rear elevational view thereof;

FIG. 17 is a top plan view thereof;

FIG. 18 is a bottom plan view thereof;

FIG. 19 is a front elevational view of a dental floss holder of a fourth preferred embodiment;

FIG. 20 is a right side elevational view of the dental floss holder illustrated in FIG. 19;

FIG. 21 is a left side elevational view thereof;

FIG. 22 is a rear elevational view thereof;

FIG. 23 is a top plan view thereof;

FIG. 24 is a bottom plan view thereof;

FIG. 25 is a front elevational view of a dental floss holder of a fifth preferred embodiment;

FIG. 26 is a right side elevational view of the dental floss holder illustrated in FIG. 25;

FIG. 27 is a left side elevational view thereof;

FIG. 28 is a rear elevational view thereof;

FIG. 29 is a top plan view thereof;

FIG. 30 is a bottom plan view thereof;

FIG. 31 is a front elevational view of a dental floss holder of a sixth preferred embodiment;

FIG. 32 is a right side elevational view of the dental floss holder illustrated in FIG. 31;

FIG. 33 is a left side elevational view thereof;

FIG. 34 is a rear elevational view thereof;

FIG. 35 is a top plan view thereof;

FIG. 36 is a bottom plan view thereof;

FIG. 37 is a perspective view of a dental floss holder of a seventh preferred embodiment;

FIG. 40 is an isometric view of a drag resistance measurement device;

DETAILED DESCRIPTION OF THE INVENTION

First Preferred Embodiment

Figure 38A:
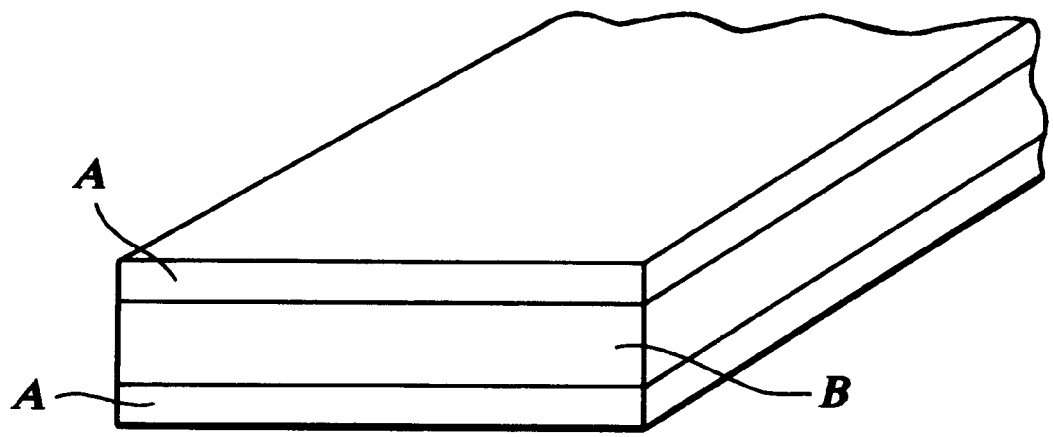
FIG. 38A is a perspective view of a dental floss according to an exemplary embodiment of this invention.

Referring now to the drawings, wherein similar reference characters designate corresponding parts throughout the several views, a first preferred embodiment of a dental floss holder the present invention is generally illustrated at 10 in FIGS. 1–6. The dental floss holder 10 includes a pair of arms, generally indicated at 12, 14, which are connected to one another by a living hinge 16.

Preferably, the arms 12, 14 are fabricated from any suitable polymeric material, such as medical grade polypropylene for use in Class 1 FDA medical devices. Dental floss 18 is connected to the arms 12, 14 so that it spans between the two arms in the manner illustrated in the drawings. The arms 12, 14 are constructed in such a way that the tension of the dental floss 18 can be adjusted so as to achieve to the aforementioned flossing method described above. Specifically, the dental floss can be manipulated to have a relatively high tension when positioning the floss between the user's teeth and a relatively low tension when flossing (i.e., wrapping the floss around the user's teeth). The dental floss 18 can also be fabricated from any suitable material, such as nylon or polytetrafluoroethylene ("PTFE"), for example. A particularly preferred dental floss is described in detail further below.

As shown, the left-hand arm 12 has a middle portion 20, a first (upper) end portion 22, and a second (lower) end portion 24. Similarly, the right-hand arm 14 has a middle portion 26, a first (upper) end portion 28, and a second (lower) end portion 30. The first end portions 22, 28 of the arms 12, 14 curve outwardly and rearwardly (see FIG. 5) away from their respective middle portions 20, 26. The dental floss 18 is attached to the upper ends of the first end portions 22, 28 of the arms 12, 14 in a manner to be described below. The construction of the first end portions 22, 28 enable the dental floss 18 to project away from the middle portions 20, 26 and the second end portions 24, 30 of the arms 12, 14, respectively, so that the dental floss can be easily positioned between the user's teeth.

Referring specifically to FIGS. 1 and 1A, the second end portions 24, 30 of the arms 12, 14 are movable between a spaced apart position (FIG. 1A) in which the second end portions of the arms diverge away from one another, and a proximate position (FIG. 1) in which the second end portions are moved toward one another. This pivoting action is achieved about the middle portions 20, 26 of the arms 12, 14 which are positioned proximate to one another by the living hinge 16 so as to define a pivot. Preferably, the living hinge 16 is approximately 0.020 inch long, and has a thickness between 0.005 inch and 0.030 inch, to create a "living hinge".

This construction results in the dental floss 18 having a first tension (e.g., relatively slack) when the second end portions 24, 30 of the arms 12, 14 are in their spaced apart position (FIG. 1A) and a second tension (e.g., relatively taut) when the second end portions are in their proximate position. Thus, when using the dental floss holder 10 of the present invention, the user can manipulate the second end portions 24, 30 to their proximate position so that the dental floss 18 is taut for moving the dental floss between the user's teeth. Upon entering the space between the teeth, the user can release the pressure applied on the second end portions 24, 30 so that they move back to their spaced apart position for loosening the tension on the dental floss 18. In this position, the dental floss 18 is sufficiently loose so that it can be wrapped about the user's teeth during flossing.

Turning now to FIG. 1B, the lower ends of the second end portions 24, 30 are provided with means of the present invention for releasably connecting the second end portions of the arms 12, 14 to one another. As shown, the left-hand arm 12 has an inwardly projecting detent 32 formed thereon. The right-hand arm 14 has a recess 34 formed therein for receiving the detent 32 of the left-hand arm 12 therein to releasably connect the second end portions 24, 30 of the arms to one another. The upper edge of the detent has several teeth 36 formed thereon which mate with teeth 38 formed on the second end portion 30 of the right-hand arm 14 within the recess 34. This construction enables the user of the dental floss holder 10 to adjust the lateral position of the arms 12, 14 for increasing the tightness of the dental floss 18. The further the detent 32 projects within the recess 34, the more the tension of the dental floss 18 increases. The teeth 36, 38 also serve the purpose of locking the arms 12, 14 relative to one another, thus enabling the user to cease applying pressure on the second end portions 24, 30 during flossing. It should be noted that any suitable release mechanism for releasing the detent 32 from the recess 34 of the second end portion 30 of the right-hand arm 14 can be provided.

Additionally, the dental floss holder 10 includes finger gripping surfaces 40 provided on the second end portions 24, 30 of the arms 12, 14. As shown, the finger gripping surfaces 40 are located adjacent the middle portions 20, 26 of the arms 12, 14, respectively. Each finger gripping surface 40 is slightly wider than the rest of the arm and includes relatively small protuberances which assist the user in gripping the arms 12, 14 of the dental floss holder 10. As best shown in FIGS. 1 and 2, these protuberances extend along the entire outer edge 42 of arm 14.

Moreover, ribs 40 are formed on the back side of the arms 12, 14 (see FIG. 4) of the dental floss holder 10 for rigidifying the arms during use. Unlike the embodiments that are discussed below, the dental floss holder 10 disclosed in FIGS. 1–6 does not flex a considerable amount, except for the first end portions 22, 28 upon applying a tightening force on the dental floss 18.

As with the other embodiments of the present invention described herein, the dental floss holder 10 is preferably fabricated by a thermal injection molding process. The dental floss 18 is attached to the first end portions 22, 28 of the arms 12, 14 by laying the dental floss within a mold (not shown) used to make the dental floss holder 10. The dental floss 18 preferably has a rectangular cross section and the first end portions 22, 28 of the arms 12, 14 are molded around the dental floss to create a mechanical attachment of the dental floss to the first end portions of the arms. Ends of the dental floss 18 are then cut off in any well known manner so that they cannot back through the openings (not shown) which receive the dental floss.

Second Preferred Embodiment

Turning now to FIGS. 7–12, there is generally indicated at 50 a dental floss holder of a second preferred embodiment. This dental floss holder 50 includes a pair of symmetrically-shaped arms generally indicated at 52, 54. The left-hand arm has a middle portion 56, a first (upper) end portion 58, and a second (lower) end portion 60. Similarly, the right-hand arm also has a middle portion 62, a first (upper) end portion 64, and a second (lower) end portion 66. A living hinge 68 is provided for connecting the middle portions 56, 62 of the arms 52, 54 to one another. As with holder 10, the first end portions 58, 64 of the dental floss holder 50 of this embodiment curve outwardly and rearwardly (see FIG. 11) away from their respective middle portions 56, 62. Dental floss 70 is attached to the upper ends of the first end portions 58, 64 of the arms 52, 54 in the same fashion described above.

The living hinge 68 prevents the over rotation of the first end portions 58, 64 upon moving the second end portions 60, 66 together. Thus, the living hinge 68 substantially precludes the snapping off of the dental floss 70 or one of the arms 52, 54 caused by applying too much pressure on the arm when moving them close together. It should be noted, however, that living hinge 68 may or may not be present in any one element of the present invention.

One major difference between dental floss holder 50 and dental floss holder 10 is that the second end portions 60, 66 of the arms 52, 54 of holder 50 are integrally formed with one another at respective terminal ends thereof. As shown, the terminal ends of the second end portions 60, 66 define a pointed member 72 which can be utilized by the user of the dental floss holder 50 to stimulate a gingival area of the user's oral cavity. In this embodiment, the arms 52, 54 are flexible; thus, the second end portions 60, 66 can be moved toward one another for increasing the tension of the dental floss 70. This results in the first end portions 58, 64 pivoting about the middle portions 56, 62 away from one another for increasing the tension of the dental floss 70.

This construction results in the dental floss 70 having a first tension (e.g., relatively slack) when the second end portions 60, 66 of the arms 52, 54 are in their relaxed condition and a second tension (e.g., relatively taut) when the second end portions are moved toward one another. Thus, when using the dental floss holder 50 of the present embodiment, the user can manipulate the second end portions 60, 66 to their proximate position so that the dental floss 70 is taut for moving the dental floss between the user's teeth. In its relaxed position, the dental floss 70 is less taut for manipulating the dental floss around the user's teeth.

Still referring to FIGS. 6–12, the dental floss holder further includes finger gripping surfaces 74 provided on the second end portions 60, 66 of the arms 52, 54 adjacent the middle portions 56, 62 of the arms. As with the finger gripping surfaces 40 of holder 10, the finger gripping surfaces 74 are slightly wider than the rest of the arms 52, 54 and include relatively small protuberances which assist the user in gripping the arms of the dental floss holder 50.

Third Preferred Embodiment

Turning now to FIGS. 13–18, a dental floss holder 80 of a third preferred embodiment is shown. This dental floss holder 80 is similar to holder 50 of FIGS. 7–12, and in this regard, corresponding parts are designated by similar reference characters throughout the views. The primary difference between holders 50 and 80 is that dental floss holder 80 has a finger gripping surface 82 which is longer in length than finger gripping surface 74 of holder 50. The increased surface area of finger surface 82 enables the user to better grasp the dental floss holder 80 when flossing.

Fourth and Fifth Preferred Embodiments

FIGS. 19–30 illustrate dental floss holders, generally designated at 90, 100, of fourth and fifth preferred embodiments, respectively. Dental floss holders 90, 100 are substantially similar to dental floss holders 50, 80, except that they lack the finger gripping surfaces 74, 72 described above. As shown, dental floss holder 90 is almost identical to holder 100, except holder 90 includes the living hinge 68, whereas holder 100 lacks this feature.

Sixth Preferred Embodiment

Turning to FIGS. 31–36, there is generally indicated at 110 a dental floss holder of a sixth preferred embodiment. As shown, this dental floss holder 110 is substantially identical to holders 50, 80 of FIGS. 7–18, but for the construction of its finger gripping surfaces 112. As shown, the finger gripping surfaces 112 project forwardly with respect to the middle portions 56, 62 and the second end portions 60, 66. This construction improves the motion of the first end portions 58, 64 upon squeezing together the second end portions 60, 66 at the finger gripping surfaces 112 for increasing the tension of the dental floss 70. Specifically, the offset nature of the finger gripping surfaces 112, upon being pressed together by the user, causes the slight forward rotation of the arms 52, 54 for ensuring that the dental floss 70 is tightened rather than loosened. As described above, the living hinge 68 prevents the over pivoting of the first end portions 58, 64 which can result from squeezing the second end portions 60, 66 too tightly together. This can result in the dental floss 70 disengaging the one of the first end portions 58, 64 thereby destroying the dental floss holder 110.

Seventh Preferred Embodiment

Lastly, turning to FIG. 37, a dental floss holder is generally indicated at 120. As shown, dental floss holder 120 comprises a yoke section generally indicated at 122 having a straight member 124 with first and second ends 126, 128, and a pair of outwardly diverging arms 130, 132 connected one another at the first end 126 of the straight member 124. The yoke section 122, at the junction of the straight member 124 and the pair of arms 130, 132, has a slot 134 formed therein, the purpose of which will be discussed in greater detail below.

A living hinge 136 is attached to the second end 128 of the straight member 124, the living hinge being constructed similarly to the living hinges described above. A pivoting member 138 is attached to the living hinge 136 and extends away from the straight member 124 of the yoke section 122 in the manner depicted in FIG. 37. The pivoting member 138 has an outwardly projecting wedge element 140, and is hingedly movable about the living hinge 136 between a first position in which the pivoting member 138 is generally parallel to the straight member 124 and a second position in which the wedge element 140 of the pivoting member 138 is moved into engagement with the straight member 124 and received within the slot 134 for moving the pair of arms 130, 132 away from one another. The reception of the wedge element 140 within the slot 134 spreads the arms 130, 132 apart.

Dental floss 142 is attached to the ends of the arms 130, 132 in the manner described above. The dental floss 142 having a first tension when the pivoting member 138 is in its first position and a second tension when the pivoting member 138 is in its second position. In this arrangement, the first tension of the dental floss 142 is less than the second tension. Thus, it should be noted that with dental floss holder 120, the tension of the dental floss 142 can be increased after initial use thereof by simply pivoting the pivoting member 138 to its second position.

In all of the exemplary embodiments of a floss holder discussed above, any suitable dental floss may be used. A preferred dental floss having sufficient properties to be firmly maintained in the ends of the arms of the floss holders discussed above includes an additive that provides sufficient drag against movement that it will not slip out of the arms. This dragf resistance is therefore a key property of the dental floss used in the floss holder. A test used to measure the drag resistance is described below.

Fumed silicon dioxide ("fumed silica") is a preferred additive, but other materials may be used, such as aluminas, titanias, aluminosilicates, sodium fluoride, stannous fluoride, monofluorophosphate, sodium carbonate, potassium carbonate, calcium carbonate, magnesium carbonate, sodium bicarbonate, potassium bicarbonate, sodium sulfate, potassium sulfate, sodium phosphate, potassium phosphate, sodium pyrophosphate, potassium pyrophosphate, particulate polytetrafluoroethylene, nylons, aramides, polyesters, phenolics, and other physically and thermally stable polymers and mixtures of any of the above.

In this aspect, the floss of the present invention comprises an improved expanded polytetrafluoroethylene (PTFE) floss material possessing inherent grippability and providing active sites for bonding medicaments, vitamins, flavors, flavorants, antioxidants, antiseptics, lubricious agents, and antilubricious agents not found in commercially available PTFE and expanded PTFE dental flosses. The floss of the present invention achieves the necessary grippability by combining a material which substantially high surface area such as fumed silica ($SiO_2$) with primary particles of PTFE before extrusion and expansion operations and optionally a calendering operation. Fumed silica morphology can be characterized by electron microscopy. Typical particles of fumed silica consist of primary particles (<25 nanometers in size) that are fused together to form aggregates. These aggregates can agglomerate to become entangled physically. The surface area of the fumed $SiO_2$ is governed by the diameter of the primary particle. Commercially available fumed silicas possess surface area in the range of 50 to 400 $meter^2$ per gram as measured by BET adsorption. The art of producing filled PTFE materials is taught in U.S. Pat. No. 5,262,234 to Minor et al. The extruded PTFE tapes which may be used for the floss of this invention are produced in accordance with the teachings of U.S. Pat. No. 3,953,566 to Gore. The tensile strength of the composite construction is increased in the direction of expansion.

Although it may have been expected that the addition of a material such $SiO_2$, which is typically used as an abrasive, would give the filled ePTFE product abrasive qualities, the inventors encountered the unexpected result that the floss of present invention containing fumed silica is tactily smooth.

The floss of the preferred embodiment achieves the necessary dimensions and strength for floss while maintaining a desirable unfolded orientation along its entire length during the expansion process as described generally in U.S. Pat. No. 5,518,012. The floss is carefully wound on spools to avoid rolling, folding or bending. Preferably, the floss comprises a minimum, unfolded, thickness of 75 μm and a minimum width of 0.7 mm. It can be appreciated that a folded orientation may be possible as well. This is less desirable, however, because width and thickness variations occur if the folding becomes inconsistent along the length of the floss article.

The floss of the present invention has numerous other advantages over presently available expanded PTFE flosses. Among the improved properties of the expanded PTFE flosses of the present invention are an open porous structure located on at least one outer surface face having active ingredients therein. This provides for increased surface friction. This may help to better disrupt the plaque layer as well as may help dislodge other oral cavity debris during flossing. It also provides the grippability of the floss so that it can be restrained in a tine element, or arm, on a flossing device such as a floss holder.

An exemplary embodiment of the floss according to the present invention is illustrated in FIG. 38A. FIG. 38A shows a 3-layer structure for the floss. Layer B is an expanded PTFE tape, and layers A sandwiching layer B are each expanded PTFE filled with approximately 10% fumed silica. Ten percent is a referred amount of fumed silica in layers A, but other amounts of fumed silica may be included as described herein.

The floss depicted in FIG. 38A is produced generally as follows. First, an expanded PTFE sheet is acquired or formed as layer B. Such material is available in a variety of forms from a number of commercial sources, such as from W. L. Gore & Associates, Inc., Elkton, Md., under the trademark GORE-TEXT®. This material may be formed as taught in U.S. Pat. No. 3,953,566 Gore, incorporated by reference. The preferred sheet comprises a thickness of about 0.5 to 1.0 mm; a density of about 0.8 to 1.5 g/cc; and a tenacity of about 0.5 to 1.0 g/tex.

Each of these properties are measured in a conventional manner. Width and thickness is determined through any conventional means, such as through the use of calipers or through measurements through a scanning electron microscope. Density is determined by dividing the measured weight of the sample by the computed volume of the sample. The volume is computed by multiplying the measured length, width, and thickness of the sample. Tenacity is calculated by dividing the sample's tensile strength by its normalized weight per unit length (tex[grams/1000 meters] or denier [grams/9000 meters]).

This expanded PTFE sheet (layer B) is then laminated on two sides to layers A of expanded PTFE containing 10% fumed $SiO_2$. These layers A are obtained by cocoagulating expanded PTFE with the 10% fumed $SiO_2$, and then extruding the cocoagulate to form a sheet as described later. The lamination of layers A to layer B may be done by any conventional lamination technique, such as calendering together using rotating rollers.

The fumed $SiO_2$ filled expanded PTFE sheets (layers A) are produced in the following manner. An aqueous dispersion of PTFE resin suitable to be subjected to a subsequent high expansion or drawing operation is blended with fumed $SiO_2$ using techniques shown in U.S. Pat. No. 5,262,234 to Minor et al.

The filled dispersion is then dried and the resulting dry cakes are broken into a finely divided powder using screens. A lubricant, such as odorless mineral spirits is blended into the screened material until a compound is formed. The volume of lubricant used should be sufficient to lubricate the primary particles of the PTFE resin so to minimize the potential of the shearing of the particles prior to extruding. The lubrication has been shown to be a special concern during the incorporation of many filler type media. Polyglycol lubricant may be used as the lubricate for a filled fine PTFE powder.

The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications a reduction ratio of 75:1 to 100:1 is preferred.

For creating a tri-layer composite construction, one unfilled extruded sheet is placed between two $SiO_2$ filled extruded sheets and are placed together one on top of the other and placed through a calendering machine having a specific gapped distance between the two rotating rollers which calendar the composite sheet. The gapped distance can range from 0.12 mm to 6.35 mm depending on the extruder reduction ratio and thus extrudate thickness. Preferably, the calendar gapped distance is between 0.254 mm to 1.5 mm using a reduction ratio within the preferred reduction ratio range.

The lubricant may then be removed by passing the coherent extrudate wet with polyglycol, over a series of rotating heated rollers or heated plates at a temperature below 325° C.

The composite slit fibers or filaments may be expanded by passing the filaments over a series of rotating heated rollers or heated plates at a temperature below 420° C. or below 325° C. but above 75° C. Preferably, over one heated plate such that the output velocity is 10% to 400% and preferably 10% to 100% faster than the filament's input velocity entering the heated plate. This corresponds to an expansion range of 1.1:1 to 5:1 longitudinally and preferably 1.1:1 to 2:1 longitudinally.

The expanded PTFE layer sheet is then processed further by passing the filaments over a second series of rotating heated rollers or heated plates at a temperature above 265° C. but preferably at or above 280° C. And over one heated plate such that the output velocity is 400% to 6500% and preferably 500% to 4500% faster than the filament's input velocity entering the heated plate. This corresponds to an expansion range of 5:1 to 66:1 in the longitundal direction and preferably 6:1 to 46:1 longitundally. The expanded PTFE filaments can be optionally longitundally expanded further if desired.

Finally, this fiber may be subjected to an amorphous locking step by exposing the fiber to a temperature in excess of 342° C.

The width of the fiber can be controlled by several process variables known in the art of expanding PTFE. Variables which can affect the width of the fiber are slit width, expansion temperatures, and expansion ratio.

The final dimensions of the fiber should comprise a width of about 0.5 to 3.0 mm; a thickness of about 50 to 250 $\mu$m; a weight/length of about 80 to 450 tex; a density of about 0.5 to 1.9 g/cc; a tensile strength of about 1.5 to 15 kg; and a tenacity of about 10 to 40 g/tex.

These measurements were made in a conventional manner. Tensile strength was measured by a tensile tester, such as an INSTRON Machine of Canton, Mass. In the case of sheet goods, the INSTRON machine was outfitted with clamping jaws which are suitable for securing the sheet goods during the measurement of tensile loading. The cross-head speed of the tensile tester was 25.4 cm per minute. The gauge length was 10.2 cm. In the case of fibers, the INSTRON machine was outfitted with fiber (yarn type) jaws that are suitable for securing fibers and strand goods during the measurement of tensile loading. The cross-head speed of the tensile tester was 25.4 cm per minute. The gauge length was 25.4 cm.

The layer B is preferably produced as follows. An expanded PTFE sheet is formed and slit into fibers of the present invention in the following manner. A fine powder PTFE resin is blended with a lubricant, such as odorless mineral spirits, until a compound is formed. The volume of lubricant used should be sufficient to lubricate the primary particles of the PTFE resin so to minimize the potential of the shearing of the particles prior to extruding.

The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications a reduction ratio of 75:1 to 100:1 is preferred.

The lubricant may then be removed, such as through volatilization, and the dry coherent extrudate is expanded in at least one direction about 1.1 to 50 times its original length (with about 1.5 to 2.5 times being preferred). Expansion may be accomplished by passing the dry coherent extrudate over a series of rotating heated rollers or heated plates.

The sheet (layer B) is then laminated on two sides to the 10% fumed $SiO_2$ layers B described above. The lamination is performed using a typical calender machine where the rollers are heated at 35° C. The combined material thickness is reduced by 10% to 80%, preferred 25–50% by calendering. Once this A-B-A composite is formed, it may be formed into a fiber by slitting it into predetermined widths by passing it between a set of gapped blades set 0.5 to 20 mm apart, or other cutting means. Following cutting, the slit composite may then be further expanded in the longitudinal direction at a ratio of 1:1 to 50:1 (with 15:1 to 35:1 being preferred) to form a fiber. This fiber may then be subjected to an amorphous locking step by exposing the fiber to a temperature in excess of 342° C. Finally, the fibers should be wound onto a spool with care taken to avoid rolling or folding of the fibers during the spooling process.

The width of the fiber can be controlled by several process variables known in the art of expanding PTFE. Variables which can affect the width of the fiber are slit width, expansion temperatures, and expansion ratio.

Figure 38B:
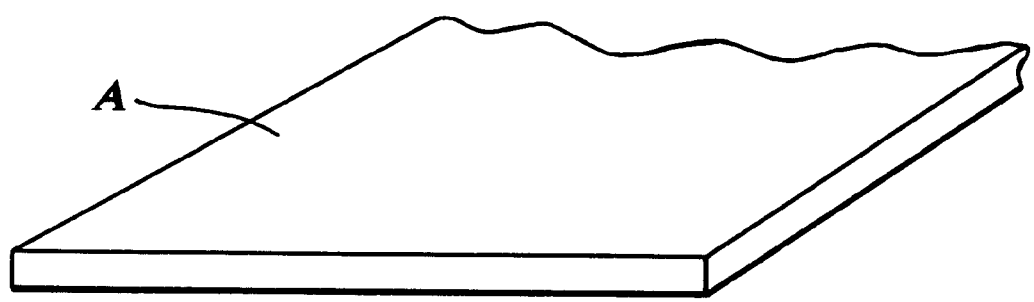
FIG. 38B is a perspective view of a dental floss according to another exemplary embodiment of this invention.

Although a tri-layer construction has been described above, the floss construction is preferrably a monolayer having a composition such as that described above for layer A, as illustrated in FIG. 38B. In this preferred embodiment, the fumed $SiO_2$ loading is between 5 and 15% by weight of fumed $SiO_2$ to filament. Alternatively, a bilayer construction (A and B) may be used.

The final dimensions of the fiber should comprise a width of about 0.5 to 3.0 mm; a thickness of about 50 to 250 $\mu$m; a weight/length of about 80 to 450 tex; a density of about 0.8 to 2.0 g/cc; a tensile strength of about 1.5 to 20 kg; and a tenacity of about 10 to 40 g/tex.

The improved properties of this invention, whereby the floss may be more securely held within the arms of the holder, can be illustrated by measuring the drag resistance of fumed silica-impregnated floss against non-impregnated floss (or floss impregnated with other materials), and by measuring the pull-out strength of such samples. The following examples and subsequent tests were performed to demonstrate these properties of the inventive.

EXAMPLES

The following examples are provided to illustrate specific embodiments of the present invention and comparative samples. They are not intended to limit the invention.

Example 1 (Tri-layer)

A composite structure consisting of two extruded $SiO_2$ filled expanded PTFE precursor tapes sandwiching one unfilled extruded PTFE tape was produced. The filled $SiO_2$ expanded PTFE tapes contained Aerosile® 380 $SiO_2$ (5% by weight of dry PTFE weight) available from the Degussa Corporation, Akron, Ohio. The silica was added to aqueous PTFE dispersion and then processed into expanded PTFE using techniques in accordance with the teachings of Minor et al., U.S. Pat. No. 5,262,234. The lubrication amount was 0.5 kilogram of polyglycol per kilogram PTFE and $SiO_2$ dry weight compound. The compounded material and extruder were isothermal at 80° C. during extruding. The extrusion pressure was 15.86 MPa over a 102 mm diameter cross-section resulting in a 11.4 liter per minute material flow rate. The extrudate dimensions were 0.76 mm thick by 152 mm wide. The unfilled PTFE tape was produced in accordance to the teachings of U.S. Pat. No. 3,953,566 to Gore using a PTFE fine powder suitable for subsequent expansion operations of greater than 200%. The PTFE powder was lubricated with an odorless mineral spirit at 0.33 cc/gram of PTFE dry weight. The compounded material and extruder were isothermal at 49° C. during extruding. The resulting tape dimensions were 0.889 mm thick by 229 mm wide.

The $SiO_2$ filled PTFE tape is calendered by running the tape between two closely spaced rotating steel rollers heated at 50° C. where the gap between the rollers results in a tape thickness of 0.241 mm. The total length of this tape was divided into two separate tape rolls of equal length being half of the original length. Using again a calendering operation, the two 0.241 mm thick $SiO_2$ filled PTFE tapes were oriented to sandwich the unfilled 0.889 mm thick PTFE tape as the three tapes entered into the calendering operation. The three tapes were thus combined together into one tape. The two steel calendering rolls were heated to 50° C. and the gap space between the two roll produce a final tape thickness of 0.813 mm.

Subsequently, the lubrication media was volatilized and removed from the combined tape or sheet producing a dry coherent extrudate layered sheet by passing the dry coherent extrudate layered sheet over a series of rotating heated rollers at a temperature of 150° C. And a second drying pass at a temperature of 270° C. The first drying pass included an expansion operation where the combined tape underwent an expansion of 100%. The dry coherent extrudate was slit to 4.3 mm widths by passing it between a set of gapped blades. The slit coherent extrudate was expanded uniaxially in the longitudinal direction over a hot plate at a temperature of 290° C. at an expansion of 1900%, a second hot plate at a temperature of 280° C. at an expansion ratio of 50%, a third hot plate at a temperature of 280° C. at an expansion ratio of 2% to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.5 mm |
| Thickness: | 0.078 mm |
| Weight/Length: | 806 denier [90 tex] |
| Density: | 0.76 g/cc |
| Tensile strength: | 2361 g |
| Tenacity: | 2.9 g/denier |

Example 2 (Trilayer)

A composite structure consisting of two extruded $SiO_2$ filled expanded PTFE precursor tapes sandwiching one unfilled extruded PTFE tape was produced. The filled $SiO_2$ expanded PTFE tapes contained Aerosil® 380 $SiO_2$ (10% by weight of dry PTFE weight) available from the Degussa Corporation, Akron, Ohio. The silica was added to aqueous PTFE dispersion and then processed into expanded PTFE using techniques in accordance to the teachings of Minor et al., U.S. Pat. No. 5,262,234. The lubrication amount was 0.5 kilogram of polyglycol per kilogram of PTFE and $SiO_2$ dry weight compound.

The compounded material and extruder were isothermal at 80° C. during extruding. The extrusion pressure was 15.86 MPa over a 102 mm diameter cross-section resulting in a 11.4 liter per minute material flow rate. The extrudate dimensions were 0.76 mm thick by 152 mm wide. The unfilled PTFE tape was produced in accordance to the teachings of U.S. Pat. No. 3,953,566 to Gore using a PTFE fine powder suitable for subsequent expansion operations of greater than 200%. The PTFE powder was lubricated with an odorless mineral spirit at 0.33 cc per gram of PTFE dry weight. The compounded material and extruder were isothermal at 49° C. during extruding. The resulting tape dimensions were 0.889 mm thick by 229 mm wide.

The $SiO_2$ filled PTFE tape is calendered by running the tape between two closely spaced rotating steel rollers heated at 50° C. where the gap between the rollers results in a tape thickness of 0.241 mm. The total length of this tape was divided into two separate tape rolls of equal length being half of the original length. Using again a calendering operation, the two 0.241 mm thick $SiO_2$ filled PTFE tapes were oriented to sandwich the unfilled 0.889 mm thick PTFE tape as the three tapes entered into the calendering operation. The three tapes were thus combined together into one tape. The two steel calendering rolls were heated to 50° C. and the gap space between the two roll produce a final tape thickness of 0.813 mm.

Subsequently, the lubrication media was volatilized and removed from the combined tape or sheet producing a dry coherent extrudate layered sheet by passing the dry coherent extrudate layered sheet over a series of rotating heated rollers at a temperature of 150° C. And a second drying pass at a temperature of 270° C. The first drying pass included an expansion operation where the combine tape underwent an expansion of 100%. The dry coherent extrudate was slit to 5.33 mm widths by passing it between a set of gapped blades. The slit coherent extrudate was expanded uniaxially in the longitudinal direction over a hot plate at a temperature of 290° C. at an expansion of 1900%, a second hot plate at a temperature of 280° C. at an expansion ratio of 50%, a third hot plate at a temperature of 280° C. at an expansion ratio of 2% to form a fiber. This fiber was subsequently subjected to an amorphous locking step and further expansion at 2% by passing the fiber over a heated plate set at a temperature of 400° C. for about 1 second.

The following measurements were taken on the finished fiber:

| | |
|---|---|
| Width: | 2 mm |
| Thickness: | 0.10 mm |
| Weight/Length: | 1407 denier [156 tex] |
| Density: | 0.78 g/cc |
| Tensile strength: | 3658 g |
| Tenacity: | 2.6 g/denier |

Example 3 (Monolayer)

A composite structure consisting of an extruded $SiO_2$ filled expanded PTFE precursor tape was produced. The filled $SiO_2$ expanded PTFE tape contained Aerosil® 380 $SiO_2$ (10% by weight of dry PTFE weight) available from the Degussa Corporation, Akron, Ohio. The silica was added to aqueous PTFE dispersion and then processed into expanded PTFE using techniques in accordance to the teachings of Minor et al., U.S. Pat. No. 5,262,234. The lubrication amount was 0.5 kilogram of polyglycol per kilogram of PTFE and $SiO_2$ dry weight compound.

The compounded material and extruder were isothermal at 80° C. during extruding. The extrusion pressure was 15.86 MPa over a 102 mm diameter cross-section resulting in a 11.4 liter per minute material flow rate. The extrudate dimensions were 0.80 mm thick by 152 mm wide.

The $SiO_2$ filled PTFE tape was calendered by running the tape between two closely spaced rotating steel rollers heated at 50° C. where the gap between the rollers results in a tape thickness of 0.76 mm.

Subsequently, the lubrication media was volatilized and removed from the tape or sheet producing a dry coherent extrudate layered sheet by passing the dry coherent extrudate layered sheet over a series of rotating heated rollers at a temperature of 150° C. And a second drying pass at a temperature of 270° C. The first drying pass included an expansion operation where the combine tape underwent an expansion of 100%. The dry coherent extrudate was slit to 4.3 mm widths by passing it between a set of gapped blades. The slit coherent extrudate was expanded uniaxially in the longitudinal direction over a hot plate at a temperature of 280° C. at an expansion of 1400%, a second hot plate at a temperature of 280° C. at an expansion ratio of 50%, a third hot plate at a temperature of 280° C. at an expansion ratio of 1% to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 2.5 mm |
| Thickness: | 0.081 mm |
| Weight/Length: | 1775 denier [197 tex] |
| Density: | 0.97 g/cc |
| Tensile strength: | 3,630 g |
| Tenacity: | 2.05 g/denier |

Example 4 (Monolaver)

A tape as specified in Example 3 after the lubrication volatilization operation was process in the following manner. The dry coherent extrudate was slit to 2.0 mm widths by passing it between a set of gapped blades. The slit coherent extrudate was expanded uniaxially in the longitudinal direction over a hot plate at a temperature of 365° C. at an expansion of 2400%. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.5 mm |
| Thickness: | 0.10 mm |
| Weight/Length: | 800 denier [89 tex] |

-continued

| | |
|---|---|
| Density: | 0.59 g/cc |
| Tensile strength: | 2,406 g |
| Tenacity: | 3.0 g/denier |

Example 5 (Monolayer)

A tape as specified in Example 3 after the lubrication volatilization operation was process in the following manner. The dry coherent extrudate was slit to 2.54 mm widths by passing it between a set of gapped blades. The slit coherent extrudate was expanded uniaxially in the longitudinal direction over a hot plate at a temperature of 380° C. at an expansion of 2400%. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.5 mm |
| Thickness: | 0.08 mm |
| Weight/Length: | 1075 denier [119 tex] |
| Density: | 0.99 g/cc |
| Tensile strength: | 3,270 g |
| Tenacity: | 3.04 g/denier |

Example 6 (Monolayer)

A composite structure consisting of an extruded $SiO_2$ filled expanded PTFE precursor tape was produced. The filled $SiO_2$ expanded PTFE tape contained Aerosil® 380 $SiO_2$ (5% by weight of dry PTFE weight) available from the Degussa Corporation, Akron, Ohio. The silica was added to aqueous PTFE dispersion and then processed into expanded PTFE using techniques in accordance to the teachings of Minor et al., U.S. Pat. No. 5,262,234. The lubrication amount was 0.5 kilogram of polyglycol per kilogram of PTFE and $SiO_2$ dry weight compound.

The compounded material and extruder were isothermal at 80° C. during extruding. The extrusion pressure was 15.86 MPa over a 102 mm diameter cross-section resulting in a 11.4 liter per minute material flow rate. The extrudate dimensions were 0.80 mm thick by 152 mm wide.

The $SiO_2$ filled PTFE tape was calendered by running the tape between two closely spaced rotating steel rollers heated at 50° C. where the gap between the rollers results in a tape thickness of 0.76 mm.

Subsequently, the lubrication media was volatilized and removed from the tape or sheet producing a dry coherent extrudate layered sheet by passing the dry coherent extrudate layered sheet over a series of rotating heated rollers at a temperature of 150° C. And a second drying pass at a temperature of 270° C. The first drying pass included an expansion operation where the combine tape underwent an expansion of 100%. The dry coherent extrudate was slit to 3.5 mm widths by passing it between a set of gapped blades. The slit coherent extrudate was expanded uniaxially in the longitudinal direction over a hot plate at a temperature of 290° C. at an expansion of 1900%, a second hot plate at a temperature of 280° C. at an expansion ratio of 50%, a third hot plate at a temperature of 280° C. at an expansion ratio of 1% to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.8 mm |
| Thickness: | 0.078 mm |
| Weight/Length: | 806 denier [135 tex] |
| Density: | 0.77 g/cc |
| Tensile strength: | 2,361 g |
| Tenacity: | 2.9 g/denier |

Comparative Example 7

(Monolayer, Dry Blending 10% (by weight) Quartz)

WO 98/01082 discloses the use of quartz ("silica") in a PTFE floss by a dry-blending technique. The inventors have discovered that PTFE floss having fumed silica surprisingly has much better grippability, or retention in floss holder tines, than quartz. Without being limited by theory, this may be due to the higher amount of surface area of fumed silica particles as compared to quartz particles, and to the morphology of fumed silica versus quartz. This Comparative Example 7 was prepared according to the disclosure in WO 98/01082.

A composite structure consisting of an extruded Quartz $SiO_2$ filled expanded PTFE precursor tape was produced. The filled $SiO_2$ expanded PTFE tape contained Quartz $SiO_2$ (10% by weight of dry PTFE weight) available from Malvarn Minerals under the name Novacite Crystalline Silica, grade L-207A. The silica was lubricated with mineral spirits and then added to a fine powder PTFE capable of expansion and then processed into expanded PTFE using techniques in accordance to the teachings of Minor et al., U.S. Pat. No. 5,262,234. The lubrication amount was 0.5 kilogram of mineral spirits per kilogram of PTFE and Quartz $SiO_2$ dry weight compound. The material was processed similarly as described in Example 3. The material processability was relatively good and the overall all linear expansion the material underwent before failure was 46:1 resulting in an average strength (tenacity) of 1.69 gram/denier (std dev. 0.105 g/d)

Comparative Example 8

(Monolayer, Dry Blending 10% (by weight) Fumed Silica)

This Comparative Example 8 was performed to demonstrate that fumed silica cannot be processed according to the disclosure in WO 98/01082.

A composite structure consisting of an extruded fumed $SiO_2$ filled expanded PTFE precursor tape was produced similarly as the example of Comparative Example 7 above however, the Quartz $SiO_2$ was replaced by fumed $SiO_2$, Aerosil® 380 $SiO_2$ (10% by weight of dry PTFE weight) available from the Degussa Corporation, Akron, Ohio. The fumed $SiO_2$ was lubricated with mineral spirits before being blended with a fine PTFE powder having the capability to undergo expansion.

The composite tape processed poorly such that it failed to undergo an expansion operation. No properties were thus measured.

Comparative Example 9

(Monolayer, Dry Blending 10% (by weight) Fumed Silica)

This Comparative Example 9 was also performed to demonstrate that fumed silica cannot be processed according to the disclosure in WO 98/01082.

A composite structure consisting of an extruded fumed $SiO_2$ filled expanded PTFE precursor tape was produced similarly as the example of Comparative Example 8 above however, the mineral spirits was added to the fine PTFE powder first and then blended with the fumed $SiO_2$, Aerosil® 380 $SiO_2$ (10% by weight of dry PTFE weight) available from the Degussa Corporation, Akron, Ohio.

The composite tape process poorly such that it failed to undergo an expansion operation. No properties were thus measured.

Comparative Example 10

(Monolayer, Dry Blending 10% (by weight) Fumed Silica)

This Comparative Example 10 was also performed to demonstrate that fumed silica cannot be processed according to the disclosure in WO 98/01082.

A composite structure consisting of an extruded fumed $SiO_2$ filled expanded PTFE precursor tape was produced similarly as the example of trial above however, the mineral spirits was added to the fine PTFE powder, CD1 from ICI Americas, Wilmington, Del., first and then blended with the fumed $SiO_2$, Aerosil®) 380 $SiO_2$ (10% by weight of dry PTFE weight) available from the Degussa Corporation, Akron, Ohio. The material processability was relatively bad and the overall all linear expansion the material underwent before failure was 2:1 resulting in an average strength (tenacity) of 0.064 gram/denier

TESTS

The following tests were performed using samples from the above examples and using additional samples mentioned below.

Drag Resistance Test

Both dynamic and static drag resistances were investigated. A simple fixture 176 as shown in FIG. 40 using three 12.7 mm (0.50 inch) diameter cylindrical shafts mounted on a rigid beam which is cantilevered from a standard tensile tester such Model 5567 by the INSTRON Company of Canton, Mass.

The fixture arm support 176 is drilled and reamed nominal 12.7 mm diameter (nominal 0.500 inch diameter) for a running fit of three cylinders 170, 172 and 174 in the fixture arm support and are secured using set-screws compressing radially on the cylinders at the cylinder—support interface. The cylinders are secured such that they do not rotate during a test iteration and extend out of the test fixture 19 mm. All three cylinders are parallel which each other and perpendicular with the cantilever fixture arm support 176. The three cylinders 170, 172 and 174 are available from McMaster-Carr Supply Company, Dayton, N.J., Part Number 8524-K24, off-white, G-7 Garolite Glass Silicon Rod material nominal 12.7 mm diameter (0.500 inch diameter). The Garolite material is parted off at nominal lengths of 19 mm.

The surface roughness ($R_a$) of the three Garolite cylinders were measured both axially and radially using the measuring apparatus, Perthometer, Model M4P available from Feinpruef Perthen, GmbH, Postfach 1853, D-3400 Goettingen, Germany. $R_a$ was measured in the cylinders' axial direction at 4 quadrants 90 degress apart measured using a stroke 0.03 inch. For the $R_a$ in the cylinders' radial direction, 3 to 4 measurements were taken using a 0.01 inch stroke randomly along the length of the cylinder. The results are presented in the table below.

| Cylinder # | $R_a$ (micro inches) | |
|---|---|---|
| | Axial | Radial |
| 1 | 93 | 55 |
| | 122 | 56 |
| | 102 | 59 |
| | 103 | |
| 2 | 32 | 101 |
| | 27 | 53 |
| | 67 | 48 |
| | 55 | 69 |
| 3 | 52 | 60 |
| | 57 | 98 |
| | 118 | 68 |
| | 66 | 40 |
| Average | 74.5 μinch | 64.3 μinch |
| Standard Deviation | 32.3 μinch | 19.2 μinch |

Before each fiber is tested, the three cylinders are removed from the fixture and placed in a cean beaker containion 99.9% isopropanol alcohol and completey submerged for 1 minute and then replaced back into the test fixture and permitted to air dry completely for 2 minutes.

The INSTRON machine model 5567 outfitted with one yarn style clamping jaw which is suitable for securing filaments during the measurement in the mode of tensile loading. The yarn style jaw was connected to a 100 Newton rated load cell 178 which was secured on the Instron's cross-head. The cross-head speed of the tensile tester was 5.4 cm per minute. The gauge length was 50 mm. The gauge length in measured from the tangent point of the yarn clamp down to the tangent point of the test specimen resting against the first of the three cylinders 170. The fixture 176 is secured to the Instron such that the test specimen secured in the yarn style clamp is perpendicular to the axis of cylinder 170. The configuration and orientation of the floss specimen around the three cylinders 170, 172 and 174 are such that there exists a wrap angle of π radians around cylinder 170, a wrap angle of π/2 radians around cylinder 172, and a wrap angle of π/2 radians around cylinder 174. Hence, a total cumulative wrap angle of π/2 radians is achieved. A distance of 25.4 mm is between cylinders 170 and 172 tangent points. A distance of 460.36 mm is between cylinders 172 and 174 tangent points.

Since the inventive material may be produced (for example as the bilayer construction) in which the longitundal surface on the top is different compared to the bottom longitundal surface, the surface which is the roughest is placed against all three cylinders. This results in placing a one turn twist in the all test specimens between cylinders 170 and 172. The test specimen has no twist between cylinders 172 and 174. The roughest surface of the present invention is easily determined tactily.

A 500 gram weight 186 is simply fixed to the end of the test specimen by tying a looped knot around the 500 gram weight and permitted come to a rest state before continuing. The length of the test specimen extending past cylinder 174 and down to the suspended 500-gram weight 186 should be at least 110 mm but less than 510 mm such that at least a test length of 110 mm is possible.

To begin the test, the Instron's cross-head is set to move upwards, thus causing the 500-gram weight to move upwards as well. The test specimen fiber slides over the three cylinders for at least a travel length of 110 mm but no more than 510 mm. The load cell is connected to a data acquisition system such that the load induced as the test specimen slides over the cylinders during the upward motion of the cross-head is recorded at a rate of at least 10 data points per second and preferably 20 points per second. The data acquisition system records the corresponding cross-head displacement during the testing as well. The drag resistance at each cross-head displacement is then calculated by the following formula:

$$e^{(\delta\theta)}=T_2/T_1$$

which reduces to:

$$\delta=[\ln(T_2/T_1)]/\theta$$

where:
- $\delta$=Drag Resistance
- $\theta$=Cumulative Wrap Angle in Radians=$2\pi$ radians
- $T_1$=average input tension=500 grams
- $T_2$=average output tension as recorded by data acquisition in gram force Note: ln is the natural logarithm base on e=2.71828 . . .

The dynamic drag resistance is determined by using the arithmetic mean-calculated drag resistance over the displacement between 10 and 20 mm.

The static drag resistance is determined by using the maximum calculated drag resistance value over the displacement between 0 and 25 mm.

To determine whether two or more materials have a statistically different drag resistance, a procedure for comparison between samples is performed. The tests were performed on samples of commercial GLIDES® Floss, available from W. L Gore & Associates, Elkton, Md., without the natural wax coating, which may be removed by soaking the floss in a heated bath at 60° C. of reagent grade isopropanol alcohol for 10 minutes and then wiping the wax away using a soft cotton cloth. The tests were also performed on samples of the inventive dental floss made according to Example 3.

1. Individual spools of the two types of test candidates (the commercial sample and the inventive sample of Example 3) were randomly chosen.
2. Fifteen 500–600 mm long samples were randomly taken from each spool and placed in individual food grade polyethylene bags and labeled. The numbers were then randomized using a standard randomization table and then run in tests using the current randomized number. The test operator was blind to the knowledge of sample labeling and randomization.
3. The samples were tested using the procedure described above.
4. Static drag resistance and mean dynamic drag resistance were measured as described above.
5. Student t-test was applied to both the mean static drag resistance and mean dynamic drag resistance data using an unpaired t-statistic with either equal or unequal variances as appropriately determined after performing an F-test on the data.
6. The drag resistances were considered different only if the t-test showed significance with 95% confidence (alpha= 0.05).

Figure 39:
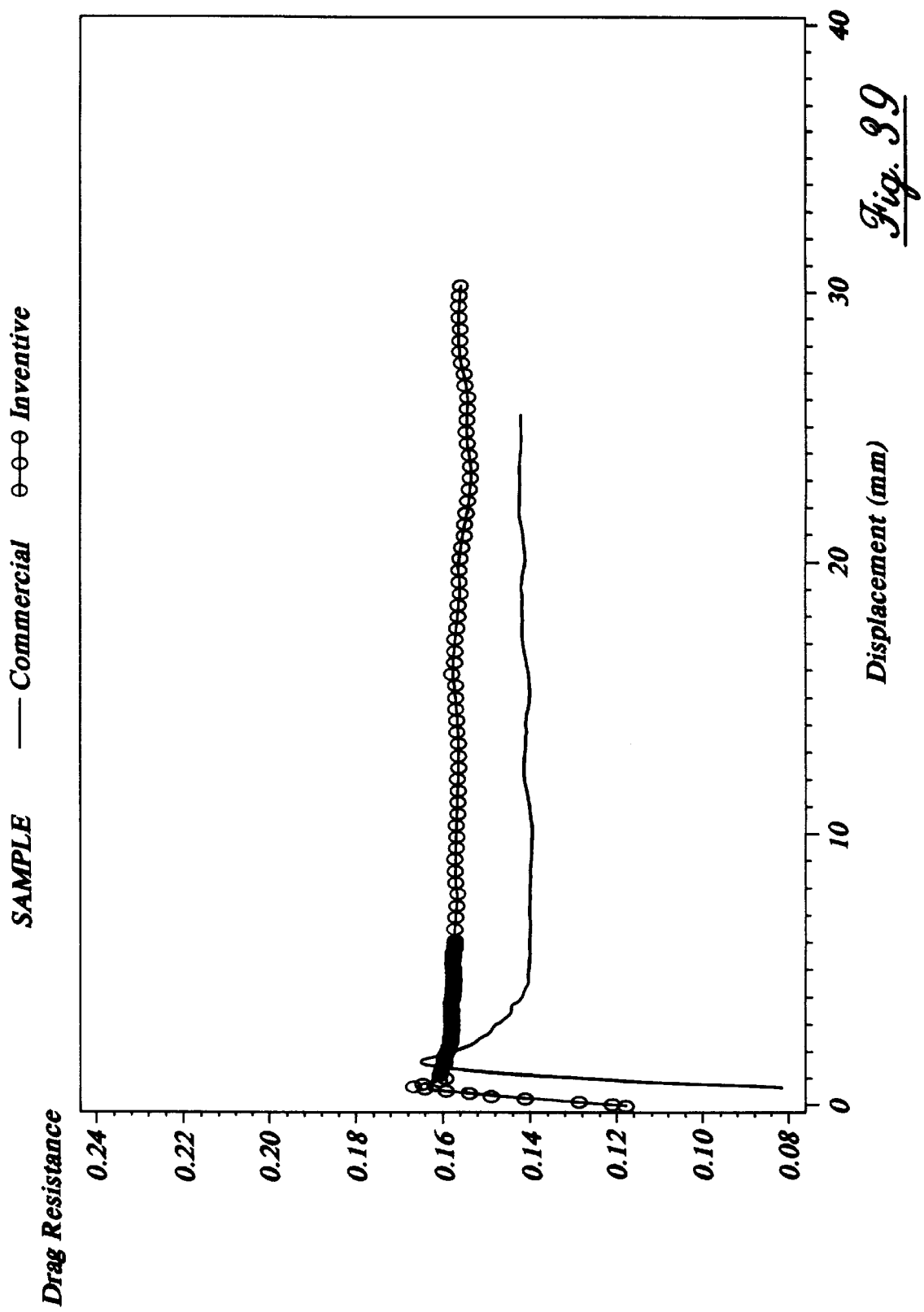
FIG. 39 is a graph of drag resistance v. displacement for an exemplary floss according to this invention and for a comparative example.

The results of these tests are shown in FIG. 39 for one representative sample of each of the two types of test specimens. The test data is summarized in the following table ("N" is the number of samples, the remaining data is the measured drag resistance.

|  | N | Mean | Std Dev. | Min. | Max |
|---|---|---|---|---|---|
| Commercial | 24 | 0.141 | 0.0007 | 0.140 | 0.142 |
| Inventive | 23 | 0.157 | 0.0004 | 0.156 | 0.158 |

As can be seen, the mean drag resistance of the inventive sample is significantly higher than the commercial sample.

Pull-Strength Measurement Test

An Instron brand tensile tester, model no. 1130, was used to measure pull-out strength. A fully prepared floss holder was used as the sample, modified as follows. Floss holders of the third embodiment discussed above were prepared of virgin commodity grade polypropylene with 2% $TiO_2$ whitening agent using an extrusion pressure of 300–450 psi and an extrusion temperature of 400–410° F. Floss holders were produced using a variety of flosses, including those according to the present invention as described in Examples #5 and #6, 10% quartz-filled expanded PTFE as described in Comparative Example #7, and commercial GLIDE® Floss, available from W. L Gore & Associates, Elkton, Md., without the natural wax coating, which may be removed by soaking the floss in a heated bath at 60° C. of reagent grade Isopropanol Alcohol for 10 minutes and then wiping the wax away using a soft cotton cloth. The floss holders were molded around the above flosses using typical insertion molding techniques in the art of thermal injection molding.

Figure 42:
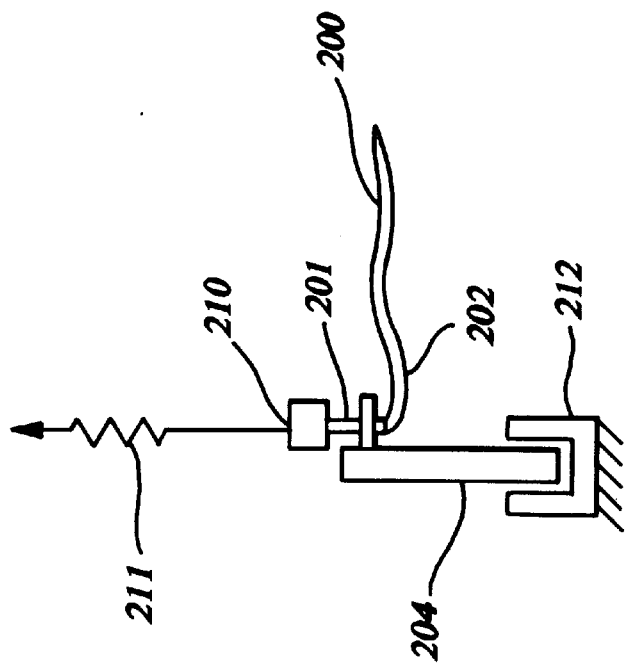
FIG. 42 is a side view of the pull-out strength measurement device of FIG. 41.
Figure 41:
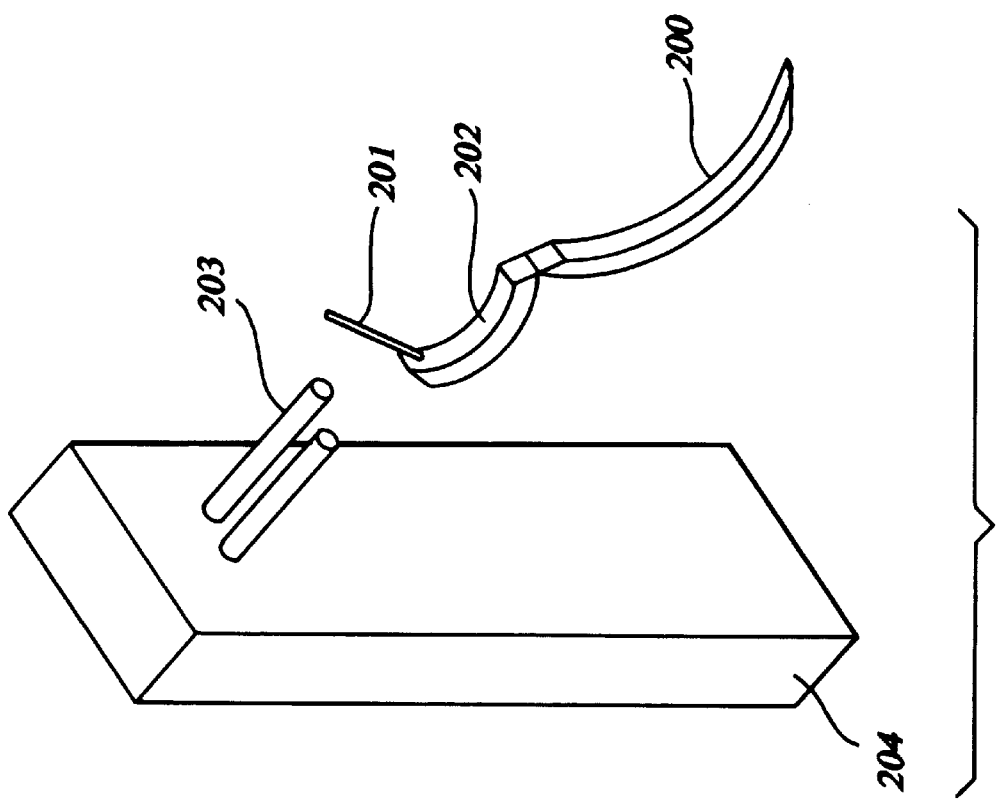
FIG. 41 is an isometric view of a pull-out strength measurement device.

For the pull-strength tests, the floss was cut at the inner face of one arm of the floss holder. The arm from which the floss was severed was broken away. As illustrated in FIGS. 41 and 42, the exposed floss 201 attached to the remaining arm 202 of the floss holder 200 was placed through two ⅛ inch diameter pins 203 (with a 0.01" space between pins 203) on a mounting block 204 so that the floss 201 extended upward through pins 203. The arm 202 remained under pins 203 as the exposed floss 201 passed through the slight space created by the two parallel ⅛ inch diameter cantilevered pins 203, hence the arm 202 and connected floss holder 200 were then restrained from any upward movement (in the direction of the cross head (not shown)) by the two pins 203. The exposed floss 201 was secured to the tensile tester's clamp 210, which was connected to a 0–25 lb. load cell 211 and cross head carriage. The applied force was measured as the carriage traveled upwards, separating floss 201 from arm 202. (Mounting block 204 was secured a bottom clamp 212 on the tensile tester machine.) The resultant force, as measured by the tensile tester's load cell 211 at the instant of the floss 201 separating from the arm 202, was collected and tabulated in the table below ("N Obs" is number of observations or tests, other recorded data is for the recorded force).

Floss Separation Data

| SAMPLE | N Obs | Mean (lbs) | Std Dev (lbs) | Minimum (lbs) | Maximum (lbs) |
|---|---|---|---|---|---|
| (Example 5) 10% Fumed | 13 | 3.62 | 0.616 | 2.50 | 4.50 |
| (Example 6) 5% Fumed | 7 | 2.58 | 0.157 | 2.40 | 2.90 |
| GLIDE ® Fiber Fiber | 6 | 0.516 | 0.204 | 0.30 | 0.90 |
| (Example 7) Quartz | 7 | 1.31 | 0.177 | 1.10 | 1.50 |

As can be seen, the mean pull strength of the inventive flosses (Examples 5 and 6) were higher than the comparative flosses. This indicates that the inventive floss is retained more securely in the floss holder than the others. This demonstrates the improved retention and grippability achievable using the inventive floss.

Although a few exemplary embodiments of the present invention have been described in detail above, those skilled in the art readily appreciate that many modifications are possible without materially departing from the novel teachings and advantages which are described herein. Specifically, for example, although the improved filament of this invention is described in the exemplary embodiments as a dental floss, the beneficial properties of the inventive filament make it useful also as a medical suture, a sewing thread, and in filter bags. Accordingly, all such modifications are intended to be included within the scope of the present invention, as defined by the following claims.

Having described the invention, what is claimed is:

1. A filament comprising expanded polytetrafluoroethylene and fumed silica, wherein said fumed silica is present in an amount no greater than 20% by weight of fumed silica to expanded polytetrafluoroethylene.

2. The filament of claim 1 wherein the filament is a dental floss.

3. The filament of claim 2 wherein said fumed silica is present in an amount of at least 1% by weight of fumed silica to expanded polytetrafluoroethylene.

4. The filament of claim 2 wherein said fumed silica is present in an amount of at least 2% by weight of fumed silica to expanded polytetrafluoroethylene.

5. The filament of claim 2 wherein said fumed silica is present in an amount of at least 3% by weight of fumed silica to expanded polytetrafluoroethylene.

6. The filament of claim 2 wherein said fumed silica is present in an amount of at least 4% by weight of fumed silica to expanded polytetrafluoroethylene.

7. The filament of claim 2 wherein said fumed silica is present in an amount of at least 5% by weight of fumed silica to expanded polytetrafluoroethylene.

8. The filament of claim 2 wherein said fumed silica is present in an amount of at least 10% by weight of fumed silica to expanded polytetrafluoroethylene.

9. The filament of claim 2 wherein said fumed silica is present in an amount of about 5% by weight of fumed silica to expanded polytetrafluoroethylene.

10. The filament of claim 2 wherein said fumed silica is present in an amount of about 10% by weight of fumed silica to expanded polytetrafluoroethylene.

11. The filament of claim 2 wherein said fumed silica is present in an amount of about 20% by weight of fumed silica to expanded polytetrafluoroethylene.

12. The filament of claim 2 wherein the filament has a strength of greater than 1 gram per denier.

13. The filament of claim 2 wherein the filament has a strength greater than 2 grams per denier.

14. The filament of claim 2 wherein the filament has a strength greater than 3 grams per denier.

15. The filament of claim 2 wherein the filament has a strength greater than 4 grams per denier.

16. The filament of claim 2 wherein the fumed silica has a primary particle size that averages less than about 25 nanometers.

17. The filament of claim 2 wherein the filament comprises a plurality of layers of expanded polytetrafluoroethylene, at least one of said layers having fumed silica disposed therein in an amount no greater than 20% by weight of fumed silica to expanded polytetrafluoroethylene.

18. The filament of claim 17 wherein the filament has an inner layer and two outer layers, at least one of said outer layers containing fumed silica in an amount no greater than 20% by weight of fumed silica to expanded polytetrafluoroethylene.

19. The filament of claim 18 wherein both of said outer layers contain fumed silica in an amount no greater than 20% by weight of fumed silica to expanded polytetrafluoroethylene.

20. The filament of claim 19 wherein said fumed silica is present in each of said outer layers in an amount of at least 2% by weight of fumed silica to expanded polytetrafluoroethylene.

21. The filament of claim 19 wherein said fumed silica is present in each of said outer layers in an amount of at least 5% by weight of fumed silica to expanded polytetrafluoroethylene.

22. The filament of claim 19 wherein said fumed silica is present in each of said outer layers in an amount of at least 10% by weight of fumed silica to expanded polytetrafluoroethylene.

23. The filament of claim 19 wherein said fumed silica is present in each of said outer layers in an amount of at least 20% by weight of fumed silica to expanded polytetrafluoroethylene.

24. The filament of claim 1 wherein the filament is a medical suture.

25. The filament of claim 1 wherein the filament is a sewing thread.

26. A filter bag comprising the filament of claim 1.

27. The filament of claim 2 wherein the fumed silica has a surface area of 50-meter$^2$ per gram or greater.

28. The filament of claim 2 wherein said filament has active sites for bonding.

29. The filament of claim 2 wherein said filament has a mean drag resistance higher than 0.141.

30. The filament of claim 29 wherein said mean drag resistance is about 0.157.

31. The filament of claim 2 wherein said filament has a mean pull strength higher than 1.31 pounds.

32. The filament of claim 31 wherein said mean pull strength is about 2.58 pounds.

33. The filament of claim 31 wherein said mean pull strength is about 3.62 pounds.

34. A dental floss holder comprising:
a pair of arms, each arm having a middle portion and first and second opposite end portions, said first end portion of each arm curving outwardly away from its respective middle portion, said middle portions of the arms being positioned proximate one another so as to define a pivot, said second end portions being movable between a first position in which the first end portions of the arms diverge away from one another, and a second position in which the first end portions are moved toward one another; and dental floss material having one end secured to the first end portion of one arm and an opposite end secured to the first end portion of the other arm, said dental floss material having a first tension when the first end portions are in their spaced apart position and a second tension when the first end portions are moved toward one another, said first tension being greater than said second tension;

wherein said dental floss material comprises a filament of expanded polytetrafluoroethylene containing fumed silica, wherein said fumed silica is present in an amount no greater than 20% by weight of fumed silica to expanded polytetrafluoroethylene.

35. The dental floss holder of claim 34 wherein said fumed silica is present in said filament in an amount of at least 1% by weight of said fumed silica to said expanded polytetrafluoroethylene.

36. The dental floss holder of claim 34 wherein said fumed silica is present in said filament in an amount of at least 5% by weight of said fumed silica to said expanded polytetrafluoroethylene.

37. The dental floss holder of claim 34 wherein said fumed silica is present in said filament in an amount of at least 10% by weight of said fumed silica to said expanded polytetrafluoroethylene.

38. The dental floss holder of claim 34 wherein said fumed silica is present in said filament in an amount of about 20% by weight of said fumed silica to said expanded polytetrafluoroethylene.

39. The dental floss holder of claim 34 wherein said fumed silica is present in said filament in an amount of about 10% by weight of said fumed silica to said expanded polytetrafluoroethylene.

40. The dental floss holder of claim 34 wherein said filament comprises a plurality of layers of expanded polytetrafluoroethylene, at least one of said layers having fumed silica disposed therein in an amount no greater than 20% by weight of fumed silica to expanded polytetrafluoroethylene.

41. The dental floss holder of claim 40 wherein said filament has an inner layer and two outer layers, at least one of said outer layers containing fumed silica in an amount no greater than 20% by weight of fumed silica to expanded polytetrafluoroethylene.

42. The dental floss holder of claim 41 wherein both of said outer layers contain fumed silica in an amount no greater than 20% by weight of fumed silica to expanded polytetrafluoroethylene.

43. The dental floss holder of claim 42 wherein said fumed silica is present in each of said outer layers in an amount of at least 2% by weight of said fumed silica to said expanded polytetrafluoroethylene.

44. The dental floss holder of claim 42 wherein said fumed silica is present in each of said outer layers in an amount of at least 5% by weight of said fumed silica to said expanded polytetrafluoroethylene.

45. The dental floss holder of claim 42 wherein said fumed silica is present in each of said outer layers in an amount of at least 10% by weight of said fumed silica to said expanded polytetrafluoroethylene.

46. The dental floss holder of claim 42 wherein said fumed silica is present in each of said outer layers in an amount of at least 20% by weight of said fumed silica to said expanded polytetrafluoroethylene.

47. A dental floss holder comprising:

a pair of arms, each arm having a middle portion and first and second opposite end portions, said first end portion of each arm curving outwardly away from its respective middle portion, said middle portions of the arms being positioned proximate one another so as to define a pivot, said second end portions being movable between a first position in which the first end portions of the arms diverge away from one another, and a second position in which the first end portions are moved toward one another; and dental floss material having one end secured to the first end portion of one arm and an opposite end secured to the first end portion of the other arm, said dental floss material having a first tension when the first end portions are in their spaced apart position and a second tension when the first end portions are moved toward one another, said first tension being greater than said second tension;

wherein said dental floss material comprises expanded polytetrafluoroethylene and fumed silica, said fumed silica being present in an amount no greater than 20% by weight of fumed silica to expanded polytetrafluoroethylene, and said dental floss material has a dynamic drag resistance of greater than about 0.142.

48. A tape comprising expanded polytetrafluoroethylene and fumed silica, wherein said fumed silica is present in an amount no greater than 20% by weight of fumed silica to expanded polytetrafluoroethylene.

* * * * *